US011740233B2

(12) United States Patent
Ashworth-Sharpe et al.

(10) Patent No.: US 11,740,233 B2
(45) Date of Patent: Aug. 29, 2023

(54) ANTIBODY-NANOPARTICLE CONJUGATES AND METHODS FOR MAKING AND USING SUCH CONJUGATES

(71) Applicant: Ventana Medical Systems, Inc., Tucson, AZ (US)

(72) Inventors: Julia Ashworth-Sharpe, Tucson, AZ (US); Christopher Bieniarz, Tucson, AZ (US); Michael Farrell, Tucson, AZ (US); Donald D. Johnson, Tucson, AZ (US); Jerome W. Kosmeder, Tucson, AZ (US); Adrian E. Murillo, Tucson, AZ (US); Chol Steven Yun, San Diego, CA (US); Zhanna Zhilina, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 16/014,965

(22) Filed: Jun. 21, 2018

(65) Prior Publication Data

US 2018/0372733 A1 Dec. 27, 2018

Related U.S. Application Data

(60) Continuation of application No. 15/263,221, filed on Sep. 12, 2016, now Pat. No. 10,031,134, which is a continuation of application No. 14/691,826, filed on Apr. 21, 2015, now Pat. No. 9,442,107, which is a division of application No. 13/640,944, filed as application No. PCT/US2011/034190 on Apr. 27, 2011, now Pat. No. 9,040,310.

(60) Provisional application No. 61/328,494, filed on Apr. 27, 2010.

(51) Int. Cl.
*G01N 33/543* (2006.01)
*G01N 33/531* (2006.01)
*G01N 33/68* (2006.01)
*G01N 33/553* (2006.01)
*C07F 9/12* (2006.01)
*C07F 9/50* (2006.01)
*C07F 9/572* (2006.01)
*C07F 9/655* (2006.01)
*G01N 33/58* (2006.01)

(52) U.S. Cl.
CPC ......... *G01N 33/54346* (2013.01); *C07F 9/12* (2013.01); *C07F 9/5004* (2013.01); *C07F 9/5022* (2013.01); *C07F 9/5045* (2013.01); *C07F 9/5728* (2013.01); *C07F 9/65515* (2013.01); *C07F 9/65517* (2013.01); *C07F 9/65522* (2013.01); *G01N 33/531* (2013.01); *G01N 33/553* (2013.01); *G01N 33/587* (2013.01); *G01N 33/6854* (2013.01); *G01N 2333/916* (2013.01)

(58) Field of Classification Search
CPC ........ C07F 9/12; C07F 9/5004; C07F 9/5022; C07F 9/5045; C07F 9/5728; C07F 9/65515; C07F 9/65522; C07F 9/65517; G01N 33/531; G01N 33/54346; G01N 33/587; G01N 33/6854; G01N 33/553; G01N 2333/916
See application file for complete search history.

(56) References Cited

U.S. PATENT DOCUMENTS

| | | |
|---|---|---|
| 5,360,895 A | 11/1994 | Hainfeld et al. |
| 5,521,289 A | 5/1996 | Hainfeld et al. |
| 5,650,327 A | 7/1997 | Copeland et al. |
| 5,654,200 A | 8/1997 | Copeland et al. |
| 6,296,809 B1 | 10/2001 | Richards et al. |
| 6,352,861 B1 | 3/2002 | Copeland et al. |
| 6,670,113 B2 | 12/2003 | Hainfeld |
| 6,827,901 B2 | 12/2004 | Copeland et al. |
| 6,921,496 B2 | 7/2005 | Anderson et al. |
| 6,943,029 B2 | 9/2005 | Copeland et al. |
| 7,632,652 B2 | 12/2009 | Bieniarz et al. |

(Continued)

FOREIGN PATENT DOCUMENTS

| | | |
|---|---|---|
| EP | 1626278 A2 | 2/2006 |
| EP | 1741717 A1 | 1/2007 |

(Continued)

OTHER PUBLICATIONS

Karyakin et al. Oriented immobilization of antibodies onto the gold surfaces via their native thiol groups. Anal. Chem. 2000, vol. 72, pp. 3805-3811. (Year: 2000).*
Sperling et al. Surface modification, functionalization and bioconjugation of colloidal inorganic nanoparticles. Phil. Trans. R. Soc. A, 2010, vol. 368, pp. 1333-1383. (Year: 2010).*
Weare et al. Improved synthesis of small phosphine-stabilized gold nanoparticles. J. Am. Chem. Soc. 2000, vol. 122, pp. 12890-12891. (Year: 2000).*

(Continued)

*Primary Examiner* — Shafiqul Hao
(74) *Attorney, Agent, or Firm* — Charney IP Law LLC; Thomas M. Finetti

(57) ABSTRACT

Disclosed herein are antibody-nanoparticle conjugates that include two or more nanoparticles (such as gold, palladium, platinum, silver, copper, nickel, cobalt, iridium, or an alloy of two or more thereof) directly linked to an antibody or fragment thereof through a metal-thiol bond. Methods of making the antibody-nanoparticle conjugates disclosed herein include reacting an arylphosphine-nanoparticle composite with a reduced antibody to produce an antibody-nanoparticle conjugate. Also disclosed herein are methods for detecting a target molecule in a sample that include using an antibody-nanoparticle conjugate (such as the antibody-nanoparticle conjugates described herein) and kits for detecting target molecules utilizing the methods disclosed herein.

19 Claims, 19 Drawing Sheets

(56) References Cited

U.S. PATENT DOCUMENTS

| | | | |
|---|---|---|---|
| 7,642,064 | B2 | 1/2010 | Bieniarz et al. |
| 2003/0211630 | A1 | 11/2003 | Richards et al. |
| 2004/0052685 | A1 | 3/2004 | Richards et al. |
| 2004/0265922 | A1 | 12/2004 | Bieniarz et al. |
| 2005/0100976 | A1 | 5/2005 | Bieniarz et al. |
| 2006/0246524 | A1* | 11/2006 | Bauer ............. A61K 49/0058 435/7.92 |
| 2007/0031337 | A1 | 2/2007 | Schulte |
| 2007/0092940 | A1* | 4/2007 | Eigenbrot ............. C07K 16/00 435/456 |
| 2007/0269594 | A1 | 11/2007 | Ackerson et al. |
| 2008/0268462 | A1 | 10/2008 | Kosmeder et al. |
| 2008/0299555 | A1 | 12/2008 | Nitta et al. |
| 2008/0318249 | A1 | 12/2008 | Powell et al. |
| 2013/0034854 | A1 | 2/2013 | Ashworth-Sharpe et al. |

FOREIGN PATENT DOCUMENTS

| | | |
|---|---|---|
| WO | 0207846 A1 | 1/2002 |
| WO | 03075961 A2 | 9/2003 |
| WO | 2004002508 A1 | 1/2004 |
| WO | 2006053225 A2 | 5/2006 |

OTHER PUBLICATIONS

Rosario et al. Disulfide bond-targeted radiolabeling: tumor specificity of a streptavidin-biotinylated monoclonal antibody complex. Cancer Res. 1990, vol. 50, pp. 804-808. (Year: 1990).*

Sun et al. Reduction—alkylation strategies for the modification of specific monoclonal antibody disulfides. Bioconjugate Chem. 2005, vol. 16, 1282-1290. (Year: 2005).*

Ackerson, C. et al. "Rigid, Specific, and Discrete Gold Nanoparticle/Antibody Conjugates," J. Am. Chem. Soc., 2006, 128, pp. 2635-2640.

Ackerson, C. et al. "Synthesis and Bioconjugation of 2 and 3 nm-Diameter Gold Nanoparticles," Bioconjugate Chem., 2010, 21, pp. 214-218.

Aubin-Tam, M-E. et al. "Structure and function of nanoparticle-protein conjugates," Biomed. Mater. 3, 2008, 034001 (17 pp).

Bieniarz, C. et al. "Extended Length Heterobifunctional Coupling Agents for Protein Conjugations," Bioconjugate Chem., 1996, 7, pp. 88-95.

Burt, J. et al. "Noble-Metal Nanoparticles Directly Conjugated to Globular Proteins," Langmuir, 2004, 20, pp. 11778-11783.

Cao, C. et al. "Signal enhancement of surface plasmon resonance immunoassay using enzyme precipitation-functionalized gold nanoparticles: A femto molar level measurement of anti-glutamic acid decarboxylase antibody," Biosensors and Bioelectronics, 22, 2007, pp. 1874-1880.

Frasco, M. et al. "Bioconjugated quantum dots and fluorescent probes for bioanalytical applications," Anal. Bioanal. Chem., 2010, 396, pp. 229-240.

Garcia Sanchez, F. et al. "Free and sol-gel immobilized alkaline phosphatase-based biosensor for the determinatino of pesticides and inorganic compounds," Analytica Chimica. Acta 484, 2003, pp. 45-51.

Gee, B. et al. "Use of an Anti-horseradish Peroxidase Antibody-Gold Complex in the ABC Technique," The Journal of Histochemisty and Cytochemistry, 1991, vol. 39, No. 6, pp. 863-869.

Hainfeld J. et al. "New Frontiers in Gold Labeling," J. Histochem. Cytochem., 2000, 48, pp. 471-480.

Fanjul-Bolado, P. et al. "Alkaline Phosphatase-Catalyzed Silver Deposition for Electrochemical Detection," Anal. Chem., 2007, 79, pp. 5272-5277.

Hwang, S. et al. "Electrochemical Detection of DNA Hybridization Using Biometallization," Anal. Chem., 2005, 77, pp. 579-584.

Kanjanawarut R. et al. "Colorimetric Detection of DNA Using Unmodified Metallic Nanoparticles and Peptide Nucleic Acid Probes," Anal Chem., 2009, 8 pages.

Lim, I-I. et al. "Gold and magnetic oxide/gold core/shell nanoparticles as bio-functional nanoprobes," Nanotechnology, 19, 2008, 305102, 11 pages.

Lyons, A. et al. "Site-specific attachment to recombinant antibodies via introduced surface cystein residues," Protein Engineering, 1990, vol. 3, No. 8, pp. 703-708.

Pohl, K. et al. "Action of Gold Chloride ("Gold Toning") on Silver-Enhanced 1 nm Gold Markers," Microscopy Research and Technique, 1998, 42, pp. 59-65.

Powell, R. et al. "Metallographic in situ hybridization," Human Pathology, 2007, 38, pp. 1145-1159.

Qu, B. et al. "A novel electrochemical immunosensor based on colabeled silica nanoparticles for determination of total prostate specific antigen in human serum," Taianta, 2008, 76, pp. 785-790.

Roth, J. et al. "Versatility of anti-horseradish peroxidase antibody-gold complexes for cytochemistry and in situ hybridization: preparation and application of soluble complexes with streptavidin-peroxidase conjugates and biotinylated antibodies," Histochemistry, 1992, 98, pp. 229-236.

Roth, J. et al. "Methods in Laboratory Investigation, Improved Accuracy in Diagnostic Immunohistochemistry, Lectin Histochemistry and In situ Hybridization Using a Gold-Labeled Horseradish Peroxidase Antibody and Silver Intensification," Laboratory Investigation, 1992. vol. 67, No. 2, pp. 263-269.

Sawada, H. et al. "A Practical Technique to Postfix Nanogold-immunolabeled Specimens with Osmium and to Embed Them in Epon for Electron Microscopy," J. Histochem. Cytochem., 2000, 48, pp. 493-498.

Shenton, W. et al. "Directed Self-Assembly of Nanoparticles into Macroscopic Materials Using Antibody-Antigen Recognition," Adv. Mater. 1999, 11, No. 6, pp. 449-452.

Szajewski, R. et al. "Rate Constants and Equilibrium Constants for Thio-Disulfide Interchange Reactions Involving Oxidized Glutathione," Journal of The American Chemical Society, 1980, 102:6, pp. 2011-2026.

Wei, H. et al. "Enzyme Colorimetric Assay Using Unmodified Silver Nanoparticles," Anal. Chem., 2008, 80, pp. 7051-7055.

Yang, X. et al. "Ultrasensitive enhanced chemiluminescence enzyme immunoassay for the determination of alpha-fetoprotein amplified by double-codified gold nanoparticle labels," Biosensors and Bioelectronics, 2009, 24, pp. 2707-2711.

Zhou, L. et al. "Aptamer-Based Rolling Circle Amplification: A Platform for Electrochemical Detection of Protein," Ana. Chem., 2007, 79, pp. 7492-7500.

Mkaline Phosphatase for Diagnostics and Life Sciences Industries brochure, Roche, Feb. 2007, 16 pages.

Kosmeder, J. et al. "Automated Alkaline Phosphatase-Catalyzed Metallographic Immunohistochemistry (IHC) and In Situ Hybridization (ISH)" poster, 95th Japanese Society of Pathology Conference, Kyoto, Japan, May 3, 2009, 1 page.

Ashworth-Sharpe, J. et al. "Automated Alkaline Phosphatase-Catalyzed Metallographic Immunohistochemistry (IHC) and In Situ Hybridization (ISH)" poster, 4th Tucson Symposium, Tucson, Arizona, Mar. 5-6, 2009, 1 page.

Zheng et al., Highly fluorescent, water-soluble, size-tunable gold quantum dots. Phys. Rev. Lett., 2004, vol. 93, No. 7, pp. 1-4.

* cited by examiner

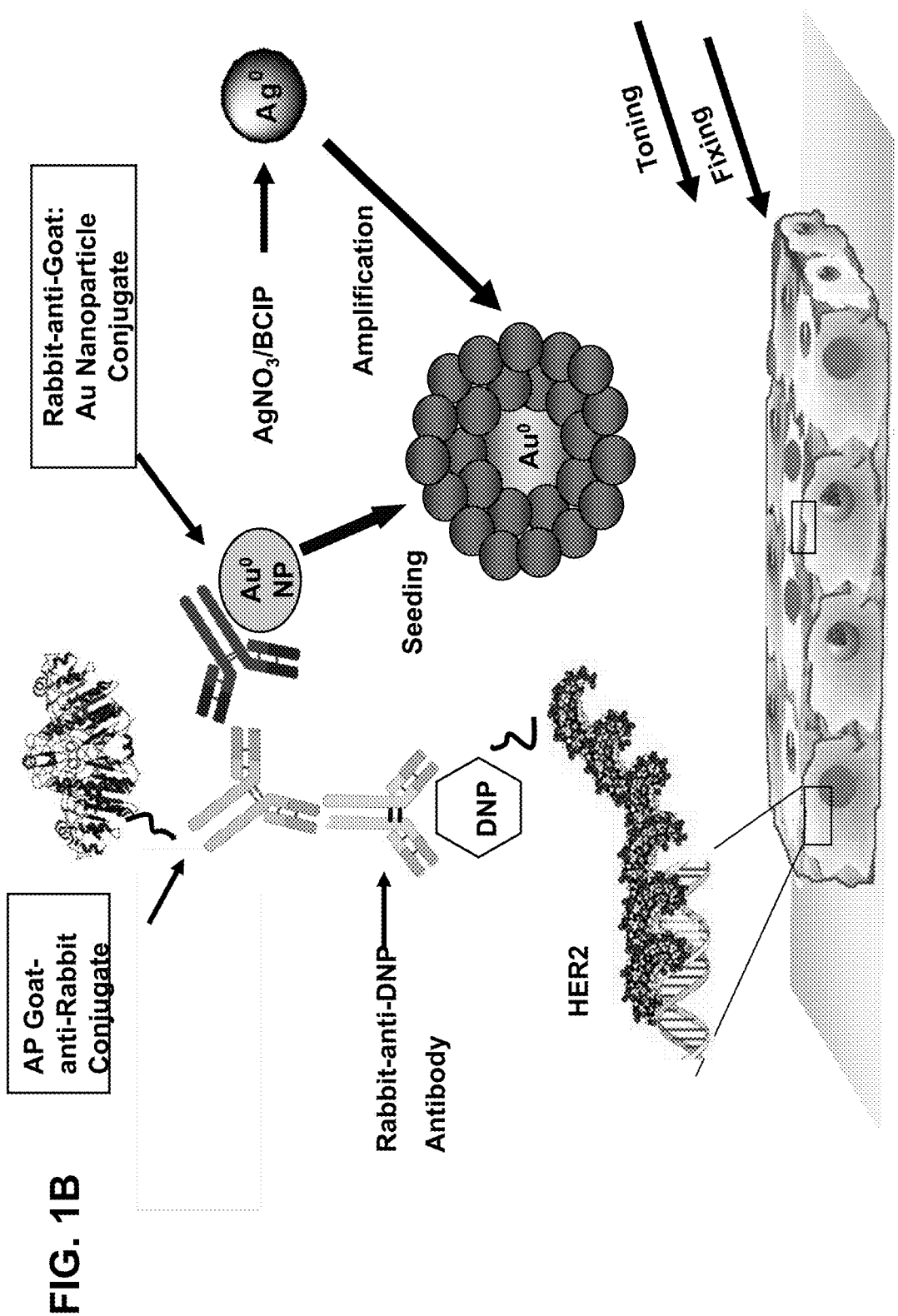

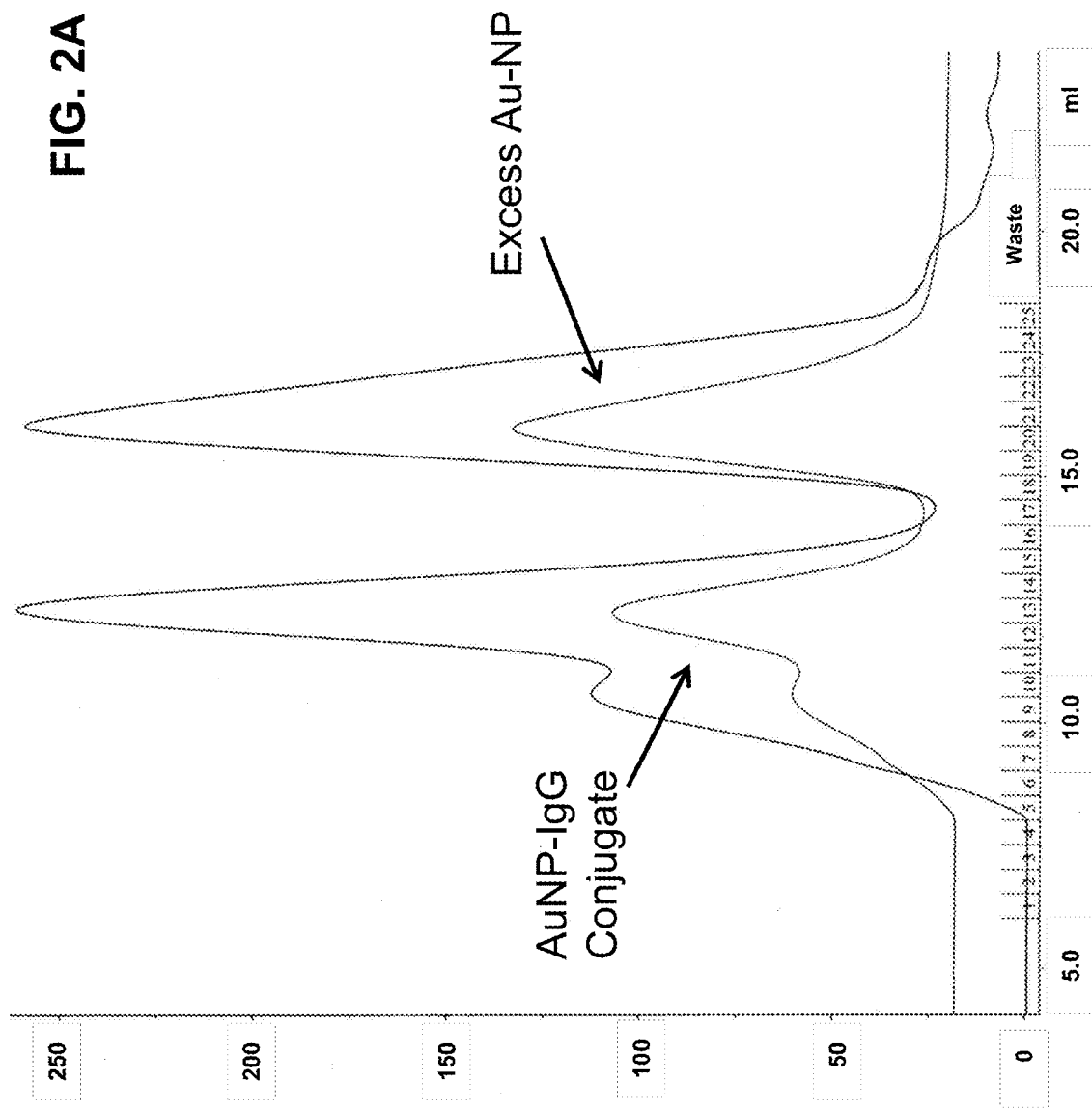

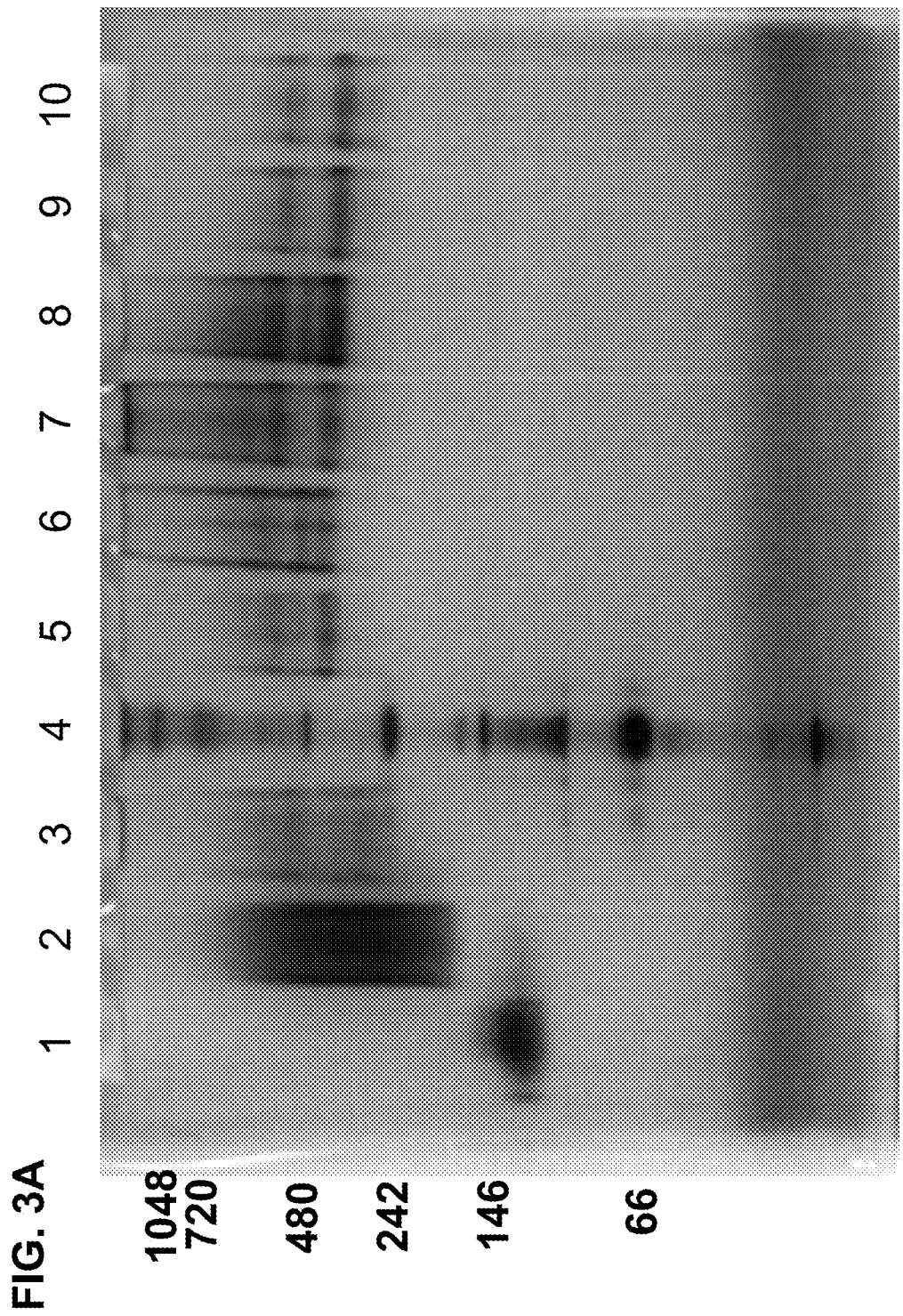

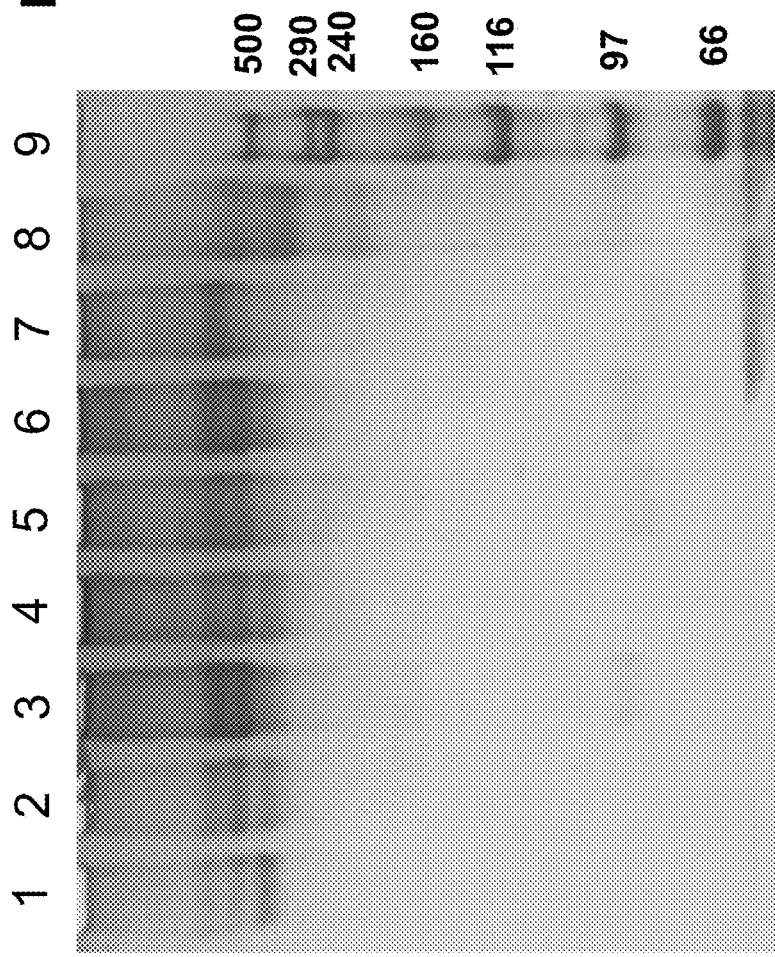

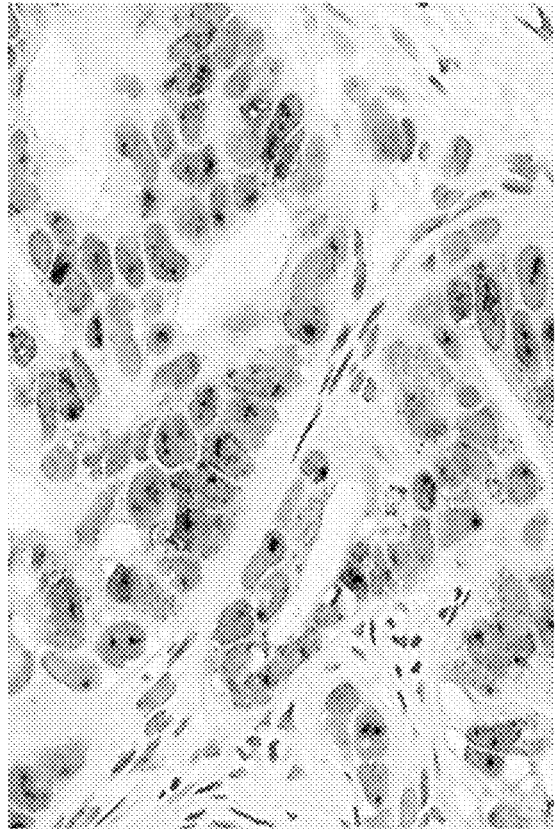
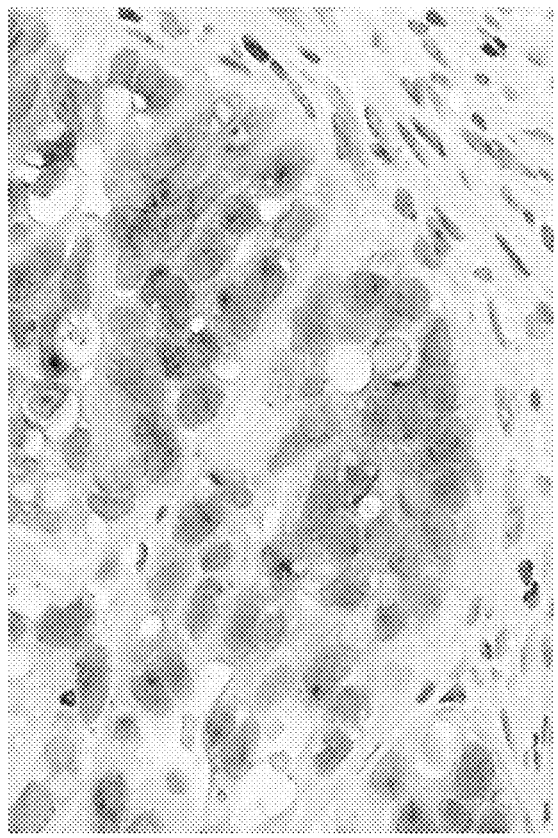
FIG. 6

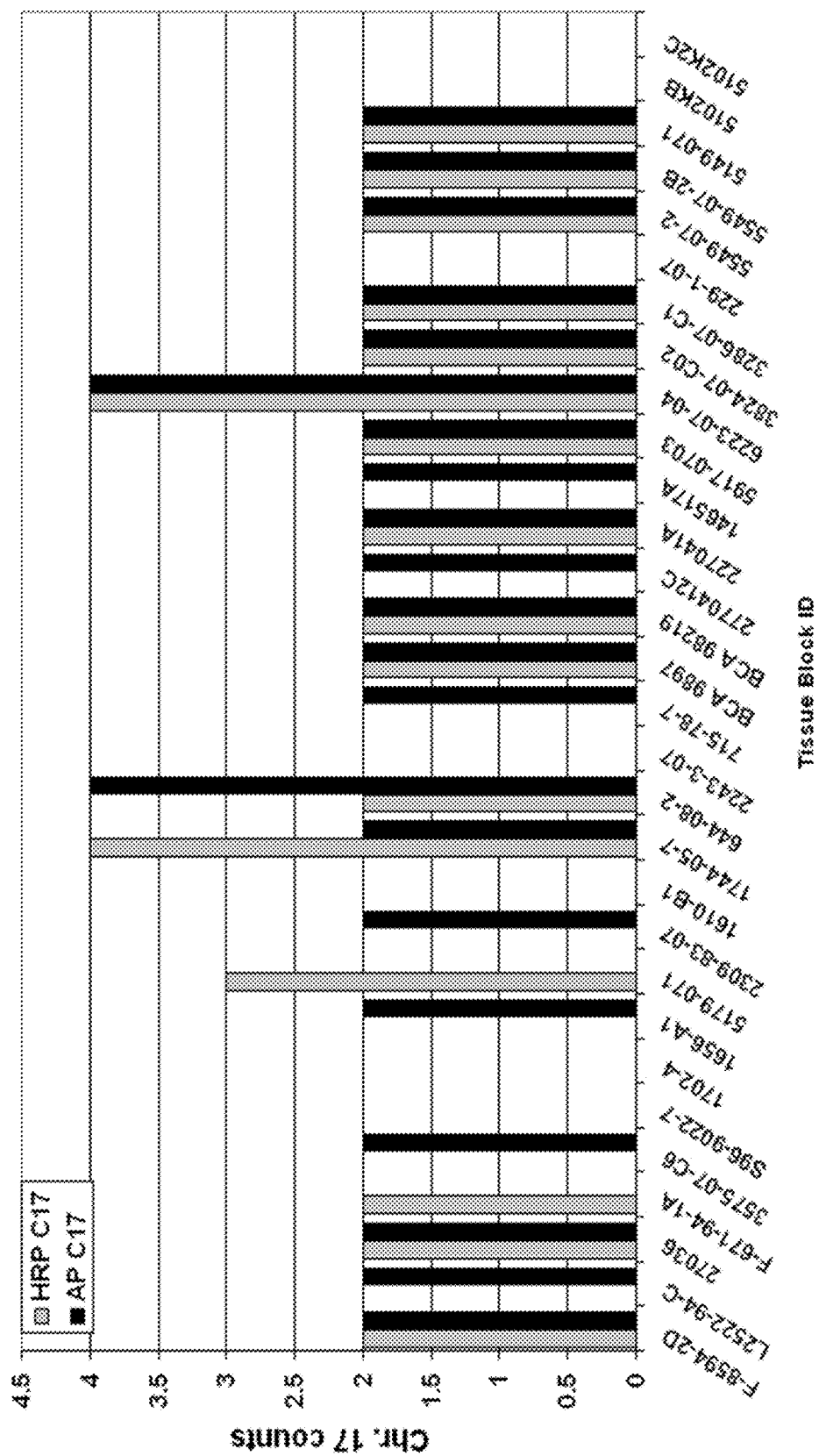

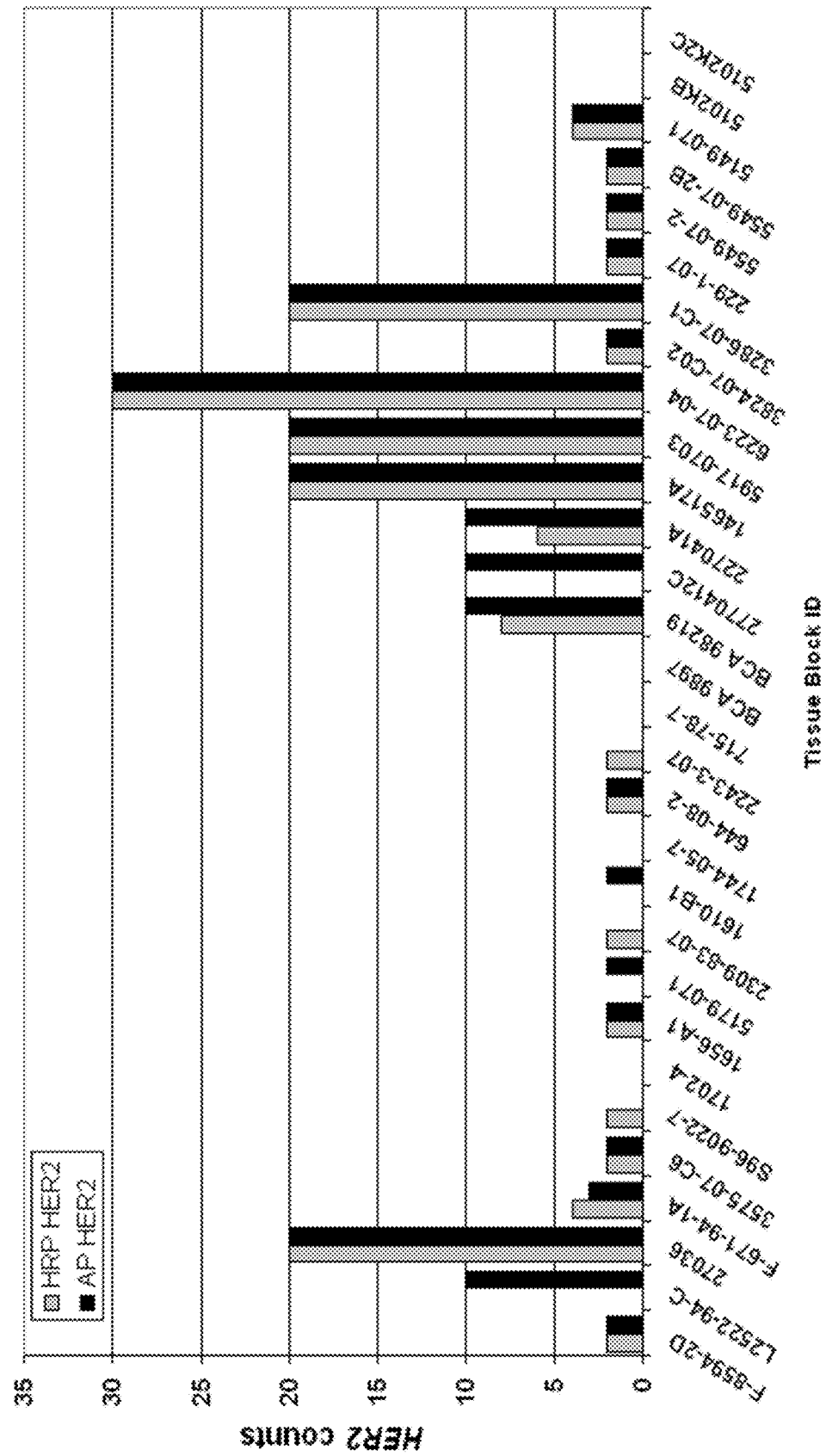

UltraView DAB
On Tonsil tissue with Bcl-2
(Bluing and Hematoxylin as counter stain)

AP-Silver
On Tonsil tissue with Bcl-2
(Nuclear Fast Red as counter stain)

AP-Silver
On Tonsil tissue with Bcl-2
(Bluing and Hematoxylin as counter stain)

ANTIBODY-NANOPARTICLE CONJUGATES AND METHODS FOR MAKING AND USING SUCH CONJUGATES

CROSS REFERENCE TO RELATED APPLICATION

The present application is continuation of U.S. patent application Ser. No. 15/263,221, filed Sep. 12, 2016, which is a continuation of U.S. patent application Ser. No. 14/691,826, filed Apr. 21, 2015, now U.S. Pat. No. 9,442,107, issued Sep. 13, 2016, which is a divisional of U.S. patent application Ser. No. 13/640,944 filed Oct. 12, 2012, now U.S. Pat. No. 9,040,310, issued May 26, 2015, is based on and claims priority to International Patent Application No. PCT/US2011/034190, filed Apr. 27, 2011, which claims the benefit of under 35 U.S.C. § 119 (e) of U.S. Provisional Patent Application No. 61/328,494, filed Apr. 27, 2010. All applications listed above are hereby incorporated by reference in their entirety.

FIELD

This disclosure relates to nanoparticle-antibody conjugates, methods for making such conjugates, and methods for their use, particularly in detecting target molecules, for example using in immunohistochemistry or in situ hybridization methods.

BACKGROUND

Immunohistochemistry (IHC) employs specific binding agents, such as antibodies, to detect an antigen of interest that may be present in a tissue sample. IHC is widely used in clinical and diagnostic applications, such as to diagnose particular disease states or conditions. For example, particular cancer types can be diagnosed based on the presence of a particular marker molecule in a sample obtained from a subject. IHC is also widely used in basic research to understand biomarker distribution and localization in different tissue parts.

Biological samples also can be examined using in situ hybridization (ISH) techniques, such as silver in situ hybridization (SISH), chromogenic in situ hybridization (CISH) and fluorescence in situ hybridization (FISH), collectively referred to as ISH. ISH is distinct from IHC, in that ISH detects nucleic acids in tissue sections, whereas IHC detects proteins.

Current silver detection systems are based upon horseradish peroxidase (HRP) technology. For SISH staining applications, hapten-labeled nucleic acid probes are targeted to specific DNA sequences in the nuclei of tissue. The probe-target complex is visualized as a dark signal on the tissue using an anti-hapten primary antibody and a secondary antibody conjugated to HRP which acts as the chromogenic enzyme. The visualization reaction is driven by sequential addition of silver acetate, hydroquinone, and hydrogen peroxide, where the HRP catalyzes the reduction of hydrogen peroxide, with the subsequent oxidation of hydroquinone. Though not entirely understood, it is postulated that in this enzymatic redox process some electrons are delivered to silver ions which are subsequently reduced to silver metal. The silver atoms precipitate in close proximity to the enzyme, forming large deposits which can be visualized as a black dot, signaling the presence of the target molecule.

SUMMARY

Current HRP SISH detection systems have several disadvantages, including inconsistent staining, non-specific seeding, and requiring a low pH buffer that can provide a media environment conducive to fungal growth. Disclosed herein is a novel, non-HRP silver detection system for detection of target molecules (including, but not limited to IHC or ISH). The methods utilize an antibody-nanoparticle conjugate and an antibody-enzyme conjugate which promote metal reduction when utilized with an appropriate substrate. Without being bound by theory, it is believed that the nanoparticle provides a nucleation site for metal deposition adjacent to the target molecule. This method provides improved sensitivity and specificity for detection of target proteins or nucleic acid molecules. The present disclosure also provides novel antibody-nanoparticle conjugates that can be utilized in the described methods and methods of making such conjugates.

The antibody-nanoparticle conjugates disclosed herein include two or more nanoparticles (such as gold, palladium, platinum, silver, copper, nickel, cobalt, iridium, or an alloy of two or more thereof) directly linked to an antibody or fragment thereof through a metal-thiol bond. In particular examples, the metal nanoparticle is conjugated to a cysteine residue of the antibody. In some examples, the conjugate includes two, three, four, five, six, seven, or more nanoparticles directly linked to an antibody. In further examples, the nanoparticles have a diameter of about 200 nm or less (for example, about 0.5 to 200 nm, about 1 nm to 100 nm, about 0.5 nm to 50 nm). In particular examples, the diameter of the nanoparticles is less than about 5 nm, for example, about 0.5 nm to 5 nm.

Methods of making the antibody-nanoparticle conjugates disclosed herein include reacting a water-soluble arylphosphine-capped nanoparticle composite with a reduced antibody to produce an antibody-nanoparticle conjugate. In some examples, the nanoparticle is gold, palladium, platinum, silver, copper, nickel, cobalt, iridium, or an alloy of two or more thereof (for example, a gold nanoparticle or a gold-palladium alloy nanoparticle). The arylphosphine-nanoparticle composite can include a sulfonated arylphosphine (for example, a mono-, bis-, or tris-sulfonated arylphosphine, such as bis-(sufonatophenyl)phenylphosphine). In some examples, the reduced antibody is formed by reacting an antibody or fragment thereof with a reducing agent (for example, dithiothreitol) to produce the reduced antibody. In particular examples, the reactant stoichiometry and/or reaction duration are modified to couple two or more nanoparticles (such as 2, 3, 4, 5, 6, 7, 8, 9, 10, or more nanoparticles) to the reduced antibody. For example, the ratio of arylphosphine-nanoparticle composite to reduced antibody is increased to increase the number of nanoparticles linked to the antibody.

Also disclosed herein are methods for detecting a target molecule in a sample that include using an antibody-nanoparticle conjugate (such as the antibody-nanoparticle conjugates described herein). In some embodiments, the method includes contacting a sample with a first antibody that binds to a target molecule (for example, a target protein or a hapten-labeled probe bound to a nucleic acid molecule); contacting the sample with a second antibody conjugated to one or more enzyme molecules, wherein the second antibody specifically binds to the first antibody; contacting the sample with a third antibody conjugated to one or more nanoparticles, wherein the third antibody specifically binds to the second antibody; contacting the sample with a substrate of the enzyme and a metal ion, such that a metal precipitate forms and colocalizes with the target molecule; and detecting the metal precipitate, thereby detecting the target molecule. In additional embodiments, the method includes contacting a sample with a first antibody conjugated to one or more enzyme molecules, wherein the first antibody binds to a target molecule (such as a target protein or hapten-labeled probe bound to a nucleic acid molecule); contacting the sample with a second antibody conjugated to one or more nanoparticles, wherein the second antibody specifically binds to the first antibody; contacting the sample with a substrate of the enzyme and a metal ion, such that a metal precipitate forms and colocalizes with the target molecule; and detecting the metal precipitate, thereby detecting the target molecule.

In some embodiments, the antibody-nanoparticle conjugate includes one or more nanoparticles (for example, 2, 3, 4, 5, 6, 7, or more nanoparticles) wherein the one or more nanoparticles include gold, palladium, platinum, silver, copper, nickel, cobalt, iridium, or an alloy of two or more thereof. In some examples, the methods include the particular antibody-nanoparticle conjugates disclosed herein. In some examples, the antibody conjugated to one or more enzyme molecules (for example, 2, 3, 4, 5, or more enzyme molecules) includes one or more alkaline phosphatase (AP), β-galactosidase, β-lactamase, glucosidase, or esterase molecules. In a particular example, the enzyme molecule is alkaline phosphatase and the enzyme substrate can be 5-bromo-3-chloro-4-indolyl phosphate, ascorbic acid phosphate, or a hydroquinone phosphate. In some examples, the metal ion includes gold, silver, copper, nickel, platinum, palladium, cobalt, or iridium.

In some embodiments, the method of detecting a target molecule further includes a gold toning step, such as contacting the sample with a gold halide salt (for example, gold chloride). In additional embodiments, the method can further include an amplification step, such as contacting the sample with a silver salt (for example, silver nitrate, silver oxide, or silver chloride). In still further embodiments, the method also includes a fixing step, including contacting the sample with a reducing agent (for example, sodium thiosulfate).

Also disclosed are kits for detecting target molecules utilizing the methods disclosed herein. For example, the kit can include one or more antibody-nanoparticle conjugates (such as an antibody-gold nanoparticle conjugate), such as the antibody-nanoparticle conjugates disclosed herein. In some examples, the kit can also include one or more antibodies coupled to one or more enzyme molecules (for example, alkaline phosphatase, such as 1 to 5 alkaline phosphatase molecules). In additional examples, the kit can also include one or more containers including a substrate for the enzyme conjugated to the antibody and one or more metal ions (for example, gold, silver, copper, nickel, platinum, palladium, cobalt, or iridium ions). The kit can optionally include reagents for additional steps, such as gold toning, silver amplification, or fixation.

The foregoing and other features of the disclosure will become more apparent from the following detailed description, which proceeds with reference to the accompanying figures.

BRIEF DESCRIPTION OF THE DRAWINGS

FIG. 1B is a schematic showing an exemplary method of in situ hybridization utilizing an antibody-nanoparticle conjugate and the methods disclosed herein.

FIG. 2A is a size exclusion chromatography trace of purification of a gold nanoparticle (AuNP)-antibody conjugate from the starting materials.

FIG. 3A is a digital image of a native polyacrylamide Novex 4-16% Bis-Tris gel used to evaluate AP-antibody conjugates synthesized with varying molar excess of MAL-dPEG™$_{12}$ NHS ester. Lane 1: AP; Lane 2: goat anti-rabbit IgG; Lane 3: goat anti-rabbit-AP conjugate (prior method); Lane 4: molecular weight markers; Lane 5: goat anti-rabbit-AP conjugate (1:3) 100× MAL, lot 1; Lane 6: goat anti-rabbit-AP conjugate (1:3) 50× MAL; Lane 7: goat anti-rabbit-AP conjugate (1:2) 100× MAL; Lane 8: goat anti-rabbit-AP conjugate (1:3) 100× MAL, lot 2; Lane 9: goat anti-rabbit-AP conjugate (1:3) 200× MAL.

FIG. 3B is a digital image of a polyacrylamide NuPAGE Novex 3-8% Tris-Acetate SDS reducing gel used to evaluate AP-antibody conjugates synthesized with varying molar excess of MAL-dPEG™$_{12}$ NHS ester. Lane 1: goat anti-rabbit-AP conjugate (1:3) 400× MAL; Lane 2: goat anti-rabbit-AP conjugate (1:3) 200× MAL; Lane 3: goat anti-rabbit-AP conjugate (1:3) 100× MAL, lot 2; Lane 4: goat anti-rabbit-AP conjugate (1:2) 100× MAL; Lane 5: goat anti-rabbit-AP conjugate (1:3) 50× MAL; Lane 6: goat anti-rabbit-AP conjugate (1:3) 100× MAL conc.; Lane 7: goat anti-rabbit-AP conjugate (recombinant) (1:3); Lane 8: goat anti-rabbit-AP conjugate; Lane 9: molecular weight markers.

FIG. 6 is a pair of digital images of ISH of Calu cell line xenografts using a HER2 riboprobe and detected with AP silver detection method without the AuNP-Ab conjugate (left) or with the AuNP-Ab conjugate (right).

DETAILED DESCRIPTION

Figure 1A:
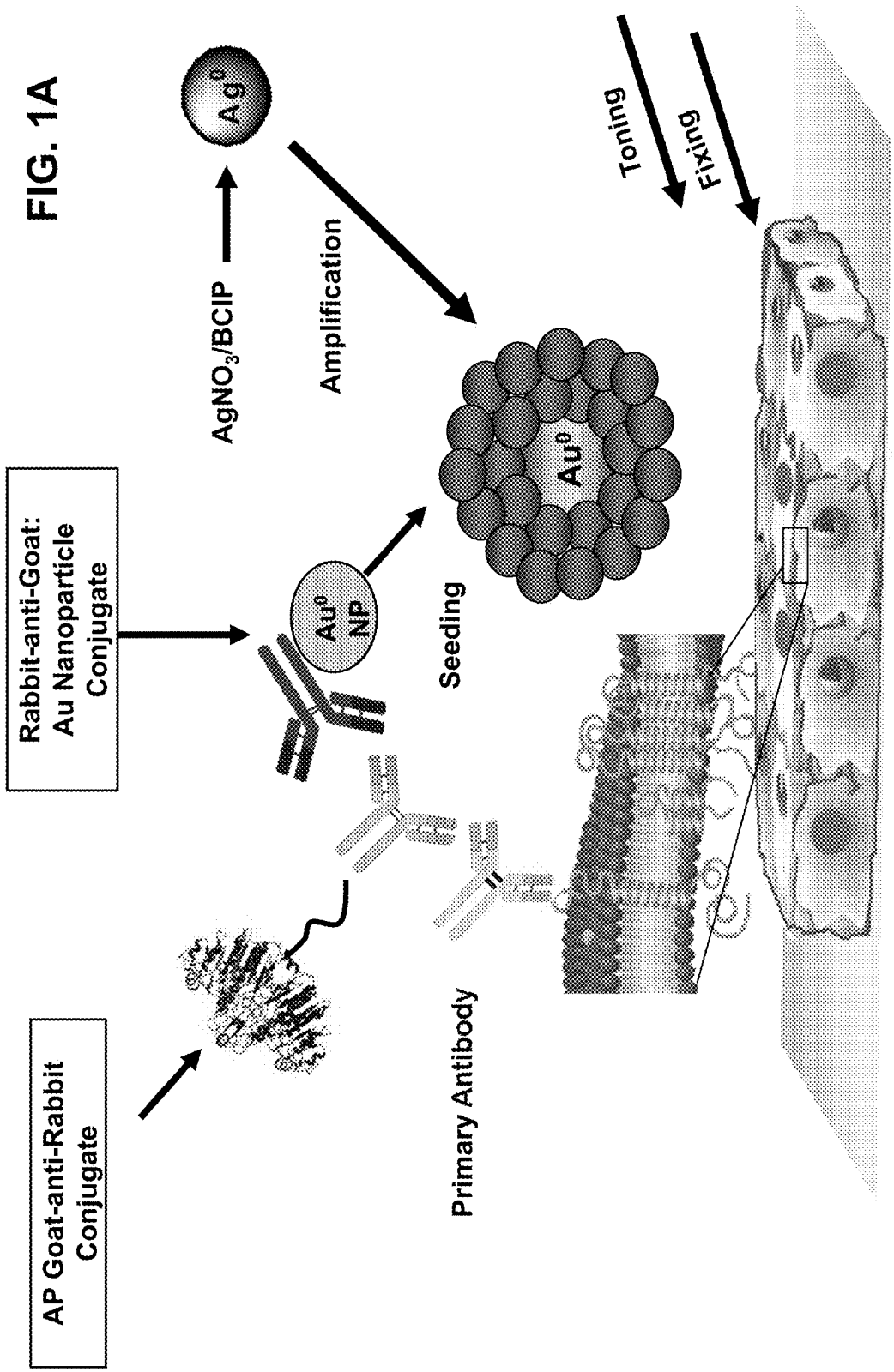
FIG. 1A is a schematic showing an exemplary method of immunohistochemistry utilizing an antibody-nanoparticle conjugate and the methods disclosed herein.

I. Abbreviations
AP: alkaline phosphatase
AuNP: gold nanoparticle
AuPdNP: gold-palladium alloy nanoparticle
BCIP: 5-bromo-4-chloro-3-indolyl phosphate
BSPP: bis-(sulfonatophenyl)phenylphosphine
DIG: digoxigenin
DNP: dinitrophenyl
DTT: dithiothreitol
HRP: horseradish peroxidase
IgG: immunoglobulin G
IHC: immunohistochemistry
ISH: in situ hybridization
NP: nanoparticle
PdNP: palladium nanoparticle
PtNP: platinum nanoparticle
SISH: silver in situ hybridization II. Terms Unless otherwise explained, all technical and scientific terms used herein have the same meaning as commonly understood by one of ordinary skill in the art to which the disclosure belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of a disclosed invention are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999.

All publications, patent applications, patents, and other references mentioned herein are incorporated by reference in their entirety for all purposes. All sequences associated with the GenBank Accession Nos. mentioned herein are incorporated by reference in their entirety as were present on Apr. 27, 2010, to the extent permissible by applicable rules and/or law.

In order to facilitate review of the various embodiments of the disclosure, the following explanations of specific terms are provided:

Alkaline phosphatase (AP): A hydrolase enzyme that removes phosphate groups from a molecule. An "alkaline phosphatase substrate" is a molecule that includes a phosphate that can be removed by alkaline phosphatase. In particular examples, an AP substrate is a molecule that becomes capable of reducing metal ions to metallic oxidation state (0) following hydrolysis of a phosphate group by AP. Examples of AP substrates include, but are not limited to, 5-bromo-4-chloro-3-indolyl phosphate (BCIP), ascorbic acid phosphate, α-tocopherol phosphate, sesamol phosphate, and eugenol phosphate.

Antibody: A polypeptide that includes at least a light chain or heavy chain immunoglobulin variable region and specifically binds an epitope of an antigen. Antibodies include monoclonal antibodies, polyclonal antibodies, or fragments of antibodies as well as others known in the art. In some examples, an antibody is linked or conjugated to another molecule, such as a nanoparticle (for example, a gold nanoparticle) or an enzyme (for example, alkaline phosphatase).

Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies) and heteroconjugate antibodies (such as, bispecific antibodies). See also, Pierce Catalog and Handbook, 1994-1995 (Pierce Chemical Co., Rockford, IL); Kuby, Immunology, 3rd Ed., W.H. Freeman & Co., New York, 1997.

A "monoclonal antibody" is an antibody produced by a single clone of B lymphocytes or by a cell into which the light and heavy chain genes of a single antibody have been transfected. Monoclonal antibodies are produced by methods known to those of ordinary skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Conjugate or Bio-conjugate: A compound having a molecule (for example, a biomolecule, such as an antibody) effectively coupled to another molecule (for example, a nanoparticle or an enzyme), either directly or indirectly, by any suitable means. In some examples, the molecule (such as an antibody) can be directly covalently coupled to a nanoparticle (such as by a metal-thiol bond). In other examples, the molecule (such as an antibody) can be coupled to an enzyme (such as alkaline phosphatase) such as by using a "linker" molecule, so long as the linker does not significantly negatively affect the activity of the enzyme or the function of the biomolecule. The linker preferably is bio-compatible. Common molecular linkers known in the art include a maleimide or succinimide group, streptavidin, neutravidin, biotin, or similar compounds.

Conjugating, joining, bonding or linking: Coupling a first unit to a second unit. This includes, but is not limited to, covalently bonding one molecule to another molecule (for example, directly or via a linker molecule), noncovalently bonding one molecule to another (e.g. electrostatically bonding) (see, for example, U.S. Pat. No. 6,921,496, which discloses methods for electrostatic conjugation), non-covalently bonding one molecule to another molecule by hydrogen bonding, non-covalently bonding one molecule to another molecule by van der Waals forces, and any and all combinations of such couplings.

Colocalize: To occur at the same or substantially the same place. In some examples, a metal precipitate (for example, metal in oxidation state 0) formed using the methods described herein colocalizes with a target molecule when it accumulates within at least about 5 µm of the target molecule (such as within at least about 1 µm, 500 nm, 250 nm, 100 nm, 50 nm, 20 nm, 10 nm, 5 nm, 2 nm, 1 nm, or 0.5 nm of the target molecule).

Contacting: Placement that allows association between two or more moieties, particularly direct physical association, for example both in solid form and/or in liquid form (for example, the placement of a biological sample, such as a biological sample affixed to a slide, in contact with an antibody or a probe).

Detect: To determine if an agent (such as a signal or particular target molecule) is present or absent, for example, in a sample. In some examples, this can further include quantification. "Detecting" refers to any method of determining if something exists, or does not exist, such as determining if a target molecule is present in a biological sample. For example, "detecting" can include using a visual or a mechanical device to determine if a sample displays a specific characteristic. In certain examples, detection refers to visually observing an antibody bound to a target molecule, or observing that an antibody does not bind to a target molecule.

Direct linkage: Coupling or conjugation of two molecules without an intervening linker. In some examples, a direct linkage is formed when an atom of a first molecule (such as an antibody) bonds to an atom of a second molecule (such as a nanoparticle). In some examples, the direct linkage is a covalent bond, such as a metal-thiol bond (for example, a gold-thiol bond).

Hapten: A molecule, typically a small molecule that can combine specifically with an antibody, but typically is substantially incapable of being immunogenic except in combination with a carrier molecule. Examples of haptens include, but are not limited to fluorescein, biotin, nitroaryls (for example, dinitrophenyl (DNP)), and digoxigenin. Additional examples of oxazole, pyrazole, thiazole, nitroaryl, benzofuran, triperpene, urea, thiourea, rotenoid, coumarin and cyclolignan haptens are disclosed in U.S. Patent Publication No. 2008/0268462.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory Press (chapters 9 and 11).

Immunohistochemistry (IHC): A method of determining the presence or distribution of an antigen (such as a protein) in a sample (for example, a portion or section of tissue) by detecting interaction of the antigen with a specific binding agent, such as an antibody. A sample including an antigen (such as a target antigen) is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). Exemplary detectable labels that can be used for IHC include, but are not limited to, radioactive isotopes, fluorochromes (such as fluorescein, fluorescein isothiocyanate, and rhodamine), and enzymes (such as horseradish peroxidase or alkaline phosphatase). In some examples, antibody-antigen binding can be detected by enzyme-promoted metallography as disclosed herein, wherein an enzyme conjugated to an antibody catalyzes transformation of a substrate to a product that can donate electrons to reduce metal ions in solution, which can subsequently be detected.

In situ hybridization (ISH): A type of hybridization that uses a labeled complementary DNA or RNA strand (a probe) to localize a specific DNA or RNA sequence in a portion or section of tissue (in situ), or, if the tissue is small enough (e.g., plant seeds, Drosophila embryos), in the entire tissue (whole mount ISH). This is distinct from immunohistochemistry, which localizes proteins in tissue sections. DNA ISH can be used to determine the structure of chromosomes, such as for use in medical diagnostics to assess chromosomal integrity. RNA ISH (hybridization histochemistry) is used to measure and localize mRNAs and other transcripts within tissue sections or whole mounts.

For hybridization histochemistry, sample cells and tissues are usually treated to fix the target transcripts in place and to increase access of the probe to the target molecule. As noted above, the probe can be a labeled complementary DNA or a complementary RNA (riboprobe). The probe hybridizes to the target sequence at elevated temperature, and then the excess probe is washed away (after prior hydrolysis using RNase in the case of unhybridized, excess RNA probe). Solution parameters, such as temperature, salt and/or detergent concentration, can be manipulated to remove most or all non-identical interactions (e.g., only sequences that are substantially identical or exact sequence matches will remain bound). Then, the labeled probe having been labeled effectively, such as with either radio-, fluorescent- or antigen-labeled bases (e.g., DNP or digoxigenin), is localized and potentially quantified in the tissue using autoradiography, fluorescence microscopy or immunohistochemistry, respectively. ISH can also use two or more probes, labeled with radioactivity or the other non-radioactive labels, such as hapten labels, and typically differentially labeled to simultaneously detect two or more transcripts.

Metal ion: Cations which require reduction and electrons for conversion to metal (zero oxidation state). In particular examples, metal ions include silver ions, gold ions, copper ions, nickel ions, platinum ions, palladium ions, cobalt ions, or iridium ions. Metal ions may be in the form of a solution of a metal salt, such as a metal nitrate, metal halide, metal acetate, or metal perchlorate (for example, silver nitrate, silver acetate, silver fluoride, or silver perchlorate). In other examples, the metal salt can include a metal sulfite, metal phosphate, or metal carbonate.

Nanoparticle: A nanoscale particle with a size that is measured in nanometers, for example, a nanoscopic particle that has at least one dimension of less than about 200 nm. Examples of nanoparticles include, by way of example and without limitation, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and quantum dots. In particular examples, a nanoparticle is a metal nanoparticle (for example, a nanoparticle of gold, palladium, platinum, silver, copper, nickel, cobalt, iridium, or an alloy of two or more thereof). Nanoparticles can include a core or a core and a shell, as in core-shell nanoparticles.

Nucleic acid molecule: A deoxyribonucleotide or ribonucleotide polymer including, without limitation, cDNA, mRNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, a nucleic acid molecule can be circular or linear.

Polypeptide or Protein: A polymer in which the monomers are amino acid residues which are joined together through amide bonds. When the amino acids are alpha-amino acids, either the L-optical isomer or the D-optical isomer can be used. The terms "polypeptide," "peptide," or "protein" as used herein are intended to encompass any amino acid sequence and include modified sequences such as glycoproteins. The term "polypeptide" or "protein" is specifically intended to cover naturally occurring proteins, as well as those which are recombinantly or synthetically produced.

Probe: An isolated nucleic acid molecule attached to a detectable label or reporter molecule, for example, a hapten. Typical labels include radioactive isotopes, enzyme substrates, cofactors, ligands, chemiluminescent or fluorescent agents, haptens (including, but not limited to, DNP), and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, Greene Publ. Assoc. and Wiley-Intersciences, 1992).

One of ordinary skill in the art will appreciate that the specificity of a particular probe increases with its length. Thus, probes can be selected to provide a desired specificity, and may comprise at least 17, 20, 23, 25, 30, 35, 40, 45, 50 or more consecutive nucleotides of desired nucleotide sequence. In particular examples, probes can be at least 100, 250, 500, 600, 1000, or more consecutive nucleic acids of a desired nucleotide sequence.

Reducing agent: An element or compound that reduces another species. In reducing another species, the reducing agent becomes oxidized, and is an electron donor. In particular examples, reducing agents include, but are not limited to dithiothreitol (DTT) and sodium thiosulfate.

Sample: The term "sample" refers to any liquid, semi-solid or solid substance (or material) in or on which a target can be present. In particular, a sample can be a biological sample or a sample obtained from a biological material. Examples of biological samples include tissue samples and cytology samples. In particular examples, the biological sample is obtained from an animal subject, such as a human subject.

A biological sample includes any solid or fluid sample obtained from, excreted by, or secreted by any living organism, including without limitation, single-celled organisms (such as bacteria, yeast, protozoans, and amoebas among others) and multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy), a xenograft, or can include a cell (whether a primary cell or cultured cell) or medium conditioned by any cell, tissue or organ. In some examples, a biological sample is a nuclear extract. In some examples, a biological sample is bacterial cytoplasm. In certain examples, a sample is a quality control sample. In other examples, a sample is a test sample. For example, a test sample is a cell, a tissue or cell pellet section prepared from a biological sample obtained from a subject. In an example, the subject is one that is at risk for or has acquired a particular condition or disease.

Specifically binds: The binding of an agent that preferentially binds or substantially only binds to a defined target (such as an antibody to a specific antigen or a nucleic acid probe to a specific nucleic acid sequence). With respect to an antigen, "specifically binds" refers to the preferential association of an antibody or other ligand, in whole or part, with a specific polypeptide. With respect to a nucleic acid sequence, "specifically binds" refers to the preferential association of a nucleic acid probe, in whole or part, with a specific nucleic acid sequence Substrate: A molecule acted upon by a catalyst, such as an enzyme (for example, alkaline phosphatase). In one example, a substrate is an alkaline phosphatase substrate, such as an aryl phosphate having the formula $RO-PO_3H_2$ or $RO-PO_3{}^{2-}(Y^+)_2$, where R is an aryl group and $Y^+$ is a cation (such as $Na^+$, $K^+$, or $Li^+$). In particular examples, an alkaline phosphatase substrate is BCIP.

Target molecule: Any molecule for which the presence, location and/or concentration is or can be determined. Examples of target molecules include proteins, nucleic acids and haptens, such as haptens covalently bonded to proteins or nucleic acid sequences. Target molecules are typically detected using one or more conjugates of a specific binding molecule and a detectable label.

III. Antibody-Nanoparticle Conjugates

Disclosed herein are antibody-nanoparticle conjugates and methods for producing such conjugates. The antibody-nanoparticle conjugates can be used in methods for detecting a target molecule (for example, a protein or a nucleic acid molecule bound to a hapten-labeled probe), such as the methods provided herein.

A. Conjugates

The antibody-nanoparticle conjugates described herein include two or more nanoparticles (such as 2, 3, 4, 5, 6, 7, 8, 9, 10, or more nanoparticles, for example, 2 to 10 nanoparticles or 2 to 7 nanoparticles) directly linked to an antibody through a metal-thiol bond between the nanoparticle and a thiol present on the antibody (such as an amino acid residue of the antibody, for example, a cysteine residue). In some embodiments, the disclosed antibody-nanoparticle conjugates are utilized in histochemical methods (such as ISH or IHC) and provide increased sensitivity over conventional methods.

In some embodiments, the nanoparticles used in the disclosed antibody-nanoparticle conjugates are metallic nanoparticles. In some examples, the nanoparticles are gold, palladium, platinum, silver, copper, nickel, cobalt, or iridium. In other examples, the nanoparticles are ruthenium, rhodium, osmium, or iron. In specific examples, the nanoparticle is a gold nanoparticle, a palladium nanoparticle, or a platinum nanoparticle. In other examples, the nanoparticles are an alloy of two or more metals (such as two or more of gold, palladium, platinum, silver, copper, nickel, cobalt, or iridium). In particular examples, the nanoparticle is a gold-palladium alloy nanoparticle. In other examples, the nanoparticle is a core-shell nanoparticle, having a metal core with a shell of a different metal (for example, a silver nanoparticle including a gold shell). In some examples, the nanoparticle has a metal core including about 10-200 atoms, for example, about 100-200, 100-150, 11-100, or 11-70 atoms.

In a particular example, the nanoparticle is a gold nanoparticle. In some examples, the gold nanoparticle has a metal core including about 10-200 gold atoms, for example, about 100-200 gold atoms, about 100-150 gold atoms, about 11-100 gold atoms, or about 11-70 gold atoms. In a particular example, the gold nanoparticle has a metal core including about 100-150 gold atoms. Metallic nanoparticles and methods for producing metallic nanoparticles are well known in the art. See, e.g., *Nanoparticles: From Theory to Application*, Gunther Schmid, ed., Wiley-BCH, 2004.

In some examples, the two or more nanoparticles conjugated to an antibody each have a diameter of from about 0.5 nm to about 200 nm (for example, about 1 nm to about 100 nm, about 2 nm to about 50 nm, about 2 nm to about 10 nm, or about 0.5 nm to about 50 nm). In particular examples, the nanoparticles have a diameter of about 5 nm or less (such as about 5 nm, about 4.5 nm, about 4 nm, about 3.5 nm, about 3 nm, about 2.5 nm, about 2 nm, about 1.5 nm, about 1 nm, or about 0.5 nm or less). In other examples, the nanoparticles have a diameter of at least about 50 nm, such as about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, or more.

The disclosed conjugates include two or more nanoparticles linked to an antibody. In some examples, the antibody can include monoclonal or polyclonal antibodies, such as IgA, IgD, IgE, IgG, or IgM; antibody fragments including, without limitation, proteolytic antibody fragments (such as $F(ab')_2$ fragments, Fab' fragments, Fab'-SH fragments, and Fab fragments as are known in the art), recombinant antibody fragments (such as sFv fragments, dsFv fragments, bispecific sFv fragments, bispecific dsFv fragments, $F(ab)'_2$ fragments, single chain Fv proteins ("scFv"), and disulfide stabilized Fv proteins ("dsFv")). In other examples, the antibody can include diabodies, triabodies, and camelid antibodies; genetically engineered antibodies (such as chimeric antibodies, for example, humanized murine antibodies); heteroconjugate antibodies (such as, bispecific antibodies); and combinations thereof. In particular examples, the antibody includes so-called "secondary antibodies," which include polyclonal antibodies with specificity for immunoglobulin (for example, IgG, IgA, or IgM) from a particular species (such as rabbit, goat, mouse, chicken, sheep, rat, cow, horse, donkey, hamster, guinea pig, or swine). In some examples, the antibody is a rabbit anti-goat IgG, a goat anti-rabbit IgG, whole human IgG, or mouse or rat antibodies. In one example disclosed herein, the antibody is a rabbit anti-goat IgG. In other examples, the antibody includes an anti-hapten antibody (such as an anti-dinitrophenyl (DNP) antibody, an anti-digoxigenin (DIG) antibody, an anti-fluorescein antibody, an anti-biotin antibody, or an anti-benzofurazan antibody).

The antibody-nanoparticle conjugates disclosed herein include a bond that directly links the antibody and the nanoparticle (for example, a linkage formed when an atom of a first molecule (such as an antibody) bonds to an atom of a second molecule (such as a nanoparticle)). In some examples, the direct linkage is a covalent bond, for example, a metal-thiol bond. In some examples, a metal atom of the nanoparticle is covalently bonded to a thiol group present in the antibody, forming a direct metal-thiol bond between the nanoparticle and the antibody. In some examples, the antibody has about 1 to 10 thiol groups (for example, 1, 2, 3, 4, 5, 6, 7, 8, 9, or 10 thiol groups), each of which can form a metal-thiol bond with a nanoparticle. In particular examples, the antibody-nanoparticle conjugate does not include a linker between the antibody and the nanoparticle.

In one example, the thiol group present in the antibody or antibody fragment is a thiol group of a cysteine amino acid residue of the antibody or antibody fragment (such as a cysteine residue present in a native antibody or a cysteine residue that is introduced in the antibody, for example, using recombinant techniques such as site-directed mutagenesis). In other examples, the thiol can be formed by reacting the antibody with a reagent that introduces a thiol group to the antibody (such as Traut's reagent (2-iminothiolane) or utilizing a protected thiol attached to activated carboxylic acid).

Immunoglobulins are tetrameric proteins composed of two identical copies of a heavy chain and two identical copies of a light chain. The four-chain structure is maintained by strong noncovalent interactions and covalent disulfide bridges between the amino-terminal half of the pairs of heavy-light chains and between the carboxyl-terminal regions of the two heavy chains. Antibodies include interchain disulfide bridges that link the heavy and light chains and also link the two heavy chains. Antibodies also include intrachain disulfide bridges that are formed within an individual light or heavy chain polypeptide. In some examples, the nanoparticles are conjugated to the antibody at thiols that are produced by reduction of intrachain disulfides of the antibody. In other examples, the nanoparticles are conjugated to the antibody at thiols that are produced by reduction of interchain disulfides of the antibody.

B. Methods for Producing Antibody-Nanoparticle Conjugates

Also disclosed herein are methods for producing the described antibody-nanoparticle conjugates. The methods provide direct conjugation of two or more nanoparticles to an antibody through thiol groups (for example, reduced native disulfide bonds) present in the antibody. The methods include reacting an arylphosphine-nanoparticle composite (for example, a nanoparticle capped with an arylphosphine)

with a reduced antibody. The arylphosphine imparts water solubility and reactivity of the nanoparticle to thiols (for example cysteine residues) present in the antibody, facilitating displacement of the arylphosphine. The use of arylphosphine also eliminates the necessity for using a powerful oxidant to activate the nanoparticle for conjugation. Finally, the conjugation can occur through reduction of existing disulfide bonds in the native protein, allowing mild reduction and preservation of the structure and function of the antibody. The number of nanoparticles conjugated to the antibody can be adjusted by the reactant stoichiometry and the number of reduced thiols present on the antibody. In some examples, the disclosed methods produce a conjugate including about two to seven nanoparticles per antibody, for example about three to seven, or about five nanoparticles per antibody. In some examples, a preparation of nanoparticle-antibody conjugates includes an average of about five nanoparticles per antibody.

The disclosed methods include reacting an arylphosphine-nanoparticle composite with a reduced antibody to produce an antibody-nanoparticle conjugate. In some embodiments, the nanoparticle is a metal nanoparticle (for example, gold, palladium, platinum, silver, copper, nickel, cobalt, iridium, or an alloy of two or more thereof). In other examples, the nanoparticle is a core-shell nanoparticle (for example, a silver nanoparticle including a gold shell). In particular examples, the nanoparticle is a gold nanoparticle, a palladium nanoparticle, or a platinum nanoparticle. In other examples, the nanoparticle is a gold-palladium alloy nanoparticle. In some examples, the nanoparticles have a diameter or from about 0.5 nm to about 200 nm (for example, about 1 nm to about 100 nm, about 2 nm to about 50 nm, about 2 nm to about 10 nm, or about 0.5 nm to about 5 nm). In particular examples, the nanoparticles have a diameter of about 5 nm or less (such as about 5 nm, about 4.5 nm, about 4 nm, about 3.5 nm, about 3 nm, about 2.5 nm, about 2 nm, about 1.5 nm, about 1 nm, or about 0.5 nm). In other examples, the nanoparticles have a diameter of at least about 50 nm, such as about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, about 200 nm, or more.

In some embodiments, the arylphosphine-nanoparticle composite is produced by reacting nanoparticles with an arylphosphine (such as a substituted arylphosphine that allows for water solubility). In some examples, the arylphosphine is soluble in water at an amount of at least 1 mg/ml (such as at least 2 mg/ml, 5 mg/ml, 10 mg/ml, 15 mg/ml, 20 mg/ml, or more). In some examples, the arylphosphine is a sulfonated phosphine (for example, mono-, bis-, or tris-sulfonated phosphine). In a particular example, the arylphosphine is bis-(sulfonatophenyl)phenylphosphine. In particular examples, the arylphosphine-nanoparticle composite is an arylphosphine-gold nanoparticle composite, such as a bis(sulfonatophenyl)phenylphosphine-gold nanoparticle composite.

In some embodiments, gold nanoparticles are produced in a liquid by reduction of chloroauric acid ($HAuCl_4$). In a particular example, a biphasic (toluene and water) sodium borohydride reduction of auric acid to an organic soluble gold nanoparticle of about 1.5-2 nm in size can be performed. This can be followed by ligand exchange with sulfonated arylphosphines in a solution of water and dichloromethane to produce water-soluble nanoparticles for conjugation with an antibody. One of skill in the art can prepare other arylphosphine-nanoparticle composites (such as palladium nanoparticle, platinum nanoparticle, or gold-palladium alloy nanoparticle composites) using similar methods and appropriate starting materials.

The disclosed methods also include reacting a reduced antibody with an arylphosphine-nanoparticle composite to produce an antibody-nanoparticle conjugate. Antibodies that can be utilized in the disclosed methods include those discussed above, for example, polyclonal antibodies, monoclonal antibodies, antibody fragments, genetically engineered antibodies (such as chimeric antibodies, for example, humanized murine antibodies), heteroconjugate antibodies (such as bispecific antibodies), and combinations thereof. In some examples, the antibody includes so-called "secondary antibodies," which include polyclonal antibodies with specificity for immunoglobulin (for example, IgG, IgA, or IgM) from a particular species (such as rabbit, goat, mouse, chicken, sheep, rat, cow, horse, donkey, hamster, guinea pig, or swine). In one specific example disclosed herein, the antibody is a rabbit anti-goat IgG. In other examples, the antibody is an anti-hapten antibody (such as an anti-DNP antibody, an anti-DIG antibody, an anti-fluorescein antibody, an anti-biotin antibody, or an anti-benzofurazan antibody). Antibodies are commercially available from numerous sources, including, but not limited to, Santa Cruz Biotechnology (Santa Cruz, Calif.), Abcam (Cambridge, Mass.), Sigma-Aldrich (St. Louis, Mo.), Life Technologies/Invitrogen (Carlsbad, Calif.), R&D Systems (Minneapolis, Minn.), BiosPacific (Emeryville, Calif.), and Abnova (Walnut, Calif.).

Methods for reducing a protein, such as an antibody, are well known to one of skill in the art. A reduced antibody for use in the methods disclosed herein can be formed by reacting an antibody with a reducing agent to produce a reduced antibody. The methods include mixing an antibody (such as an antibody or antibody fragment) with a reducing agent for a sufficient period of time to produce a reduced antibody. The reduced antibody includes one or more (such as 1, 2, 3, 4, 5, 6, or more) available thiol groups. In some examples, the available thiol groups are produced as a result of the reduction of disulfide bonds present in the native antibody (for example, one or more intrachain disulfide or interchain disulfide). In particular examples, the available thiol groups are produced by reduction of at least one intrachain disulfide bridge present in the native antibody.

In some examples, the reducing agent is a mono- or dithiol reducing agent (for example, 2-mercaptoethanol, 2-mercaptoethylamine, cysteine, reduced glutathione, dithiothreitol, dithioerythritol, glycol dimercaptoacetate, or thioglycolic acid). In another example, the reducing agent is a trialkylphosphine reducing agent (for example, tris(2-carboxyethyl)phosphine). A suitable concentration of reducing agent and time for the reaction can be determined by titrating the number of thiols produced in a given amount of time with a particular concentration of reducing agent at a particular temperature. The number of thiols available can be determined by one of skill in the art (for example, by Ellman's assay; Ellman, *Arch. Biochem. Biophys.* 82:70-77, 1959). In some examples, the amount of reducing agent is about 1 mM to about 1 M (for example, about 1 mM to 500 mM, about 5 mM to 100 mM, or about 10 mM to 50 mM) and the amount of time is about 10 minutes to about 24 hours (for example, about 10 minutes to 2 hours or about 20 minutes to 60 minutes). In a particular, non-limiting example, an antibody is reacted with about 0.5 M dithiothreitol (DTT) for about 25 minutes at 4° C. to produce a reduced antibody.

In some examples, the arylphosphine-nanoparticle composite and the reduced antibody are incubated for at least about 2 hours (for example, 2, 3, 4, 5, 6, 8, 10, 12, 16, 18, 24, 36, 48, 60, 72 hours or more). In additional examples, the reaction of the arylphosphine-nanoparticle composite and the reduced antibody is carried out at a temperature of about 2° C. to about 28° C. (for example, about 4° C. to about 25° C., about 10° C. to about 22° C.). In some examples, the reaction is carried out at about 4° C. In other examples, the reaction is carried out at room temperature (for example, about 22° C. to about 26° C.). In particular examples, the reaction is carried out at about 4° C. for 48 hours or at room temperature for about 24 hours. One of skill in the art will understand that the reaction time and temperature can be varied. For example, less nanoparticle conjugation to the antibody may occur in reactions of shorter duration (such as less than 24 hours) or at colder temperature (such as 4° C.), whereas more nanoparticle conjugation to the antibody may occur in reactions of longer duration (such as more than 24 hours) or at higher temperature (such as room temperature).

In some embodiments, the number of nanoparticles coupled to the antibody in the antibody-nanoparticle conjugate is controlled by adjusting the reactant stoichiometry and/or reaction duration. In some examples, by increasing the amount of the arylphosphine-nanoparticle composite included in the reaction with the reduced antibody, conjugates including two or more nanoparticles (such as 2, 3, 4, 5, 6, 7, 8, 9, 10, or more) coupled to an antibody molecule can be produced. Such embodiments include those having non-integer ratios of nanoparticles to antibody. In some examples, the antibody-nanoparticle conjugate includes 2, 2.5, 3, 3.5, 4, 4.5, 5, or more nanoparticles per antibody. In other examples, the antibody-nanoparticle conjugate includes an average of about two to seven (such as about three to six, or about five) nanoparticles per antibody. In some examples, the reactant stoichiometry of arylphosphine-nanoparticle composite to reduced antibody is about 2:1, 3:1, 4:1, 5:1, 6:1, 7:1, 8:1, 9:1, 10:1, or more. In one non-limiting example, the reaction stoichiometry is about 5 mg arylphosphine-nanoparticle composite to about 1.5 mg of antibody and the resulting antibody-nanoparticle conjugate includes about 3.5 nanoparticles per antibody. In another non-limiting example, the reaction stoichiometry is about 10 mg arylphosphine-nanoparticle composite to about 1.5 mg of antibody and the resulting antibody-nanoparticle conjugate includes about 5 nanoparticles per antibody.

In additional embodiments, the number of nanoparticles coupled to the antibody in the antibody-nanoparticle conjugate is controlled by adjusting the number of reduced thiols present on the reduced antibody in the reaction. Methods for controlling reduction of a protein are known to one of skill in the art. In some examples, the type or amount of reducing agent and/or the duration of the reduction reaction are adjusted to control the degree of reduction of the protein. For example, by increasing the amount of reducing agent and/or the duration of the reaction, a greater number of disulfides in the protein are reduced, producing more reduced thiols, and allowing for conjugation of a greater number of nanoparticles to a single antibody molecule. Conversely, by decreasing the amount of reducing agent and/or the duration of the reaction, fewer disulfides in the protein are reduced, producing fewer reduced thiols, and allowing for conjugation of a fewer number of nanoparticles to a single antibody molecule.

IV. Methods of Using Antibody-Nanoparticle Conjugates

Disclosed herein are methods for detecting a target molecule in a sample that utilize antibody-nanoparticle conjugates, including the antibody-nanoparticle conjugates described herein. The methods include detecting a target molecule, such as histochemical methods, for example, immunohistochemistry (IHC) and in situ hybridization (ISH) methods. The antibody-nanoparticle conjugates can increase the sensitivity and/or specificity of IHC and ISH methods over conventional methods.

The methods described herein utilize an antibody-nanoparticle conjugate as a nucleation center for enzyme-promoted metallography. In this process, an enzyme catalyzes the chemical transformation of a substrate to a product that can subsequently donate electrons to reduce metal ions in solution. Without being bound by theory, it is believed that in the methods disclosed herein the resulting metal atoms nucleate at the nanoparticle surface, increasing the size of the particle to a degree that it can be visualized, for example, by light microscopy. The antibody-nanoparticle conjugate appears to provide a specific point of the metal atom deposit, resulting in increased signal with low background staining In some embodiments, the methods disclosed herein include contacting a sample with a first antibody that binds to a target molecule; contacting the sample with a second antibody conjugated to one or more enzyme molecules, wherein the second antibody specifically binds the first antibody; contacting the sample with a third antibody conjugated to one or more nanoparticles (such as an antibody-nanoparticle conjugate disclosed herein), wherein the third antibody specifically binds the second antibody; contacting the sample with a substrate of the enzyme and a metal ion, such that a metal precipitate forms and colocalizes with the target molecule; and detecting the metal precipitate. FIG. 1 shows schematic diagrams of exemplary, non-limiting, methods disclosed herein for performing IHC (FIG. 1A) and ISH (FIG. 1B) utilizing antibody-nanoparticle conjugates.

In other embodiments, one or more of the antibodies utilized in the disclosed methods may include a hapten (such as DNP, DIG, fluorescein, biotin, or benzofurazan), and the antibody that specifically binds the antibody is an anti-hapten antibody. In one example, the methods include contacting a sample with a first antibody that binds to a target molecule, wherein the first antibody includes a hapten; contacting the sample with a second antibody conjugated to one or more enzyme molecules, wherein the second antibody specifically binds the hapten of the first antibody; contacting the sample with a third antibody conjugated to one or more nanoparticles, wherein the third antibody specifically binds to the second antibody; contacting the sample with a substrate of the enzyme and a metal ion, such that a metal precipitate forms and colocalizes with the target molecule; and detecting the metal precipitate. In other examples, the antibody conjugated to one or more enzyme molecules (e.g., the second antibody) includes a hapten and the antibody conjugated to one or more nanoparticles is an anti-hapten antibody that specifically binds the hapten of the second antibody. In some embodiments, the first and/or second antibodies include a hapten and the second and/or third antibodies are anti-hapten antibodies. In some examples, when more than one of the antibodies utilized in the disclosed methods includes a hapten, the haptens are different haptens.

In other embodiments, the methods disclosed herein include contacting a sample with a first antibody conjugated to one or more enzyme molecules, wherein the first antibody binds to a target molecule; contacting the sample with a second antibody conjugated to one or more nanoparticles (such as an antibody-nanoparticle conjugate disclosed herein), wherein the second antibody specifically binds the first antibody; contacting the sample with a substrate of the enzyme and a metal ion, such that a metal precipitate forms and colocalizes with the target molecule; and detecting the metal precipitate. In further embodiments, the methods include contacting a sample with a first antibody conjugated to one or more enzyme molecules, wherein the first antibody binds to a target molecule and wherein the first antibody includes a hapten (such as DNP, DIG, fluorescein, biotin, or benzofurazan); contacting the sample with a second antibody conjugated to one or more nanoparticles, wherein the second antibody is an anti-hapten antibody that specifically binds the hapten of the first antibody; contacting the sample with a substrate of the enzyme and a metal ion, such that a metal precipitate forms and colocalizes with the target molecule; and detecting the metal precipitate.

In some examples, a metal precipitate (for example, metal in oxidation state 0) formed using the methods described herein colocalizes with a target molecule. For example, the metal precipitate accumulates within at least about 5 μm of the target molecule (such as within at least about 1 μm, 500 nm, 250 nm, 100 nm, 50 nm, 20 nm, 10 nm, 5 nm, 2 nm, 1 nm, or 0.5 nm of the target molecule).

In some examples, the disclosed methods are methods for detecting a target molecule that is a protein (for example, IHC methods) and the antibody that binds to the target molecule is an antibody that specifically binds one or more epitopes in the target protein (sometimes referred to as a "primary" antibody). In other examples, the disclosed methods are methods for detecting a target molecule that is a nucleic acid molecule (for example, ISH methods) and the antibody that binds to the target molecule is an anti-hapten antibody that specifically binds a hapten-labeled nucleic acid probe, which specifically binds the target nucleic acid molecule. Target molecules are discussed in Section VI, below.

In additional embodiments, the methods disclosed herein can be used in conjunction with non-metallographic detection methods (such as colorimetric or fluorescent detection methods) to detect additional target molecules. In some examples, multiple detectable labels that can be separately detected can be conjugated to different specific binding molecules (such as antibodies) that specifically bind different targets to provide a multiplexed assay that can provide detection of multiple targets in a sample. For example, the methods disclosed herein can be used to detect a target molecule (such as a target protein or nucleic acid molecule) in a sample. The sample can also be subjected to colorimetric methods, for example, use of an antibody conjugated to an enzyme that produces a chromogen when used with an appropriate substrate (such as HRP with 3,3'-diamionbenzidine (DAB) or AP with BCIP/nitro-blue tetrazolium (NBT)) to detect a second or subsequent target molecule. The sample can also be subjected to fluorescent detection methods, for example an antibody conjugated to a fluorescent molecule (such as fluoresceins, luminophores, coumarins, BODIPY dyes, resorufins, rhodamines, or quantum dots) to detect a second or subsequent target molecule. Alternatively, a sample could be subjected to colorimetric and/or fluorescent detection methods to detect one or more target molecules, followed by the methods disclosed herein to detect an additional target molecule. The appropriate order for multiplexing (for example, IHC prior to ISH in most examples) can be determined by one of skill in the art utilizing routine methods.

The methods described herein include detecting the metal precipitate (for example, metal in oxidation state zero), such as metal precipitate nucleated at the surface of a nanoparticle in the antibody-nanoparticle conjugates included in the disclosed methods. The metal precipitate may be detected visually, such as by brightfield microscopy. In some examples, the use of the antibody-nanoparticle conjugate allows detection and quantitation of a low copy number nucleic acid molecule (such as a nucleic acid molecule present at about 1-3 copies per cell) or a low abundance protein to be detected without a conventional signal amplification step (such as tyramide signal amplification, which is typically required).

A person of ordinary skill in the art will appreciate that embodiments of the methods disclosed herein for detection of one or more target molecules can be automated. Ventana Medical Systems, Inc. is the assignee of a number of United States patents disclosing systems and methods for performing automated analyses, including U.S. Pat. Nos. 5,650,327; 5,654,200; 6,296,809; 6,352,861; 6,827,901; and 6,943,029, and U.S. published application Nos. 2003/0211630 and 2004/0052685.

A. Antibody-Enzyme Conjugates

The disclosed methods include an antibody conjugated to one or more enzyme molecules. In some examples, the antibody conjugated to one or more enzyme molecules is an antibody that specifically binds to an antibody that in turn binds to a target molecule (sometimes referred to as a "secondary antibody"). In other examples, the antibody conjugated to one or more enzyme molecules is an antibody that binds to a target molecule or a hapten-labeled nucleic acid probe bound to a target nucleic acid molecule (sometimes referred to as a "primary antibody"). In still further examples, the one or more enzyme molecules are conjugated to an anti-hapten antibody (such as an anti-DNP antibody, an anti-DIG antibody, an anti-fluorescein antibody, an anti-biotin antibody, or an anti-benzofurazan antibody).

The enzyme conjugated to the antibody in the disclosed methods is an enzyme capable of transforming a redox-inactive enzyme substrate to produce at least one product capable of reducing metal ions to metal in a zero oxidation state.

In some examples, the enzyme can be an alkaline phosphatase (AP), acid phosphatase, β-galactosidase, β-lactamase (such as a cephalosporinase or penicillinase), glucosidase (such as an α- or β-glucosidase), or esterase. The enzyme-antibody conjugate includes one or more enzyme molecules (such as 2, 3, 4, 5, 6, 7, 8, 9, 10, or more enzyme molecules). In some examples, the enzyme-antibody conjugate includes about 2-10 enzyme molecules, such as about 2-8 enzymes molecules, for example 3-5 enzyme molecules. In particular non-limiting examples, the enzyme-antibody conjugate includes two or three enzyme molecules. Antibody-enzyme conjugates and methods of producing such conjugates are well known in the art. In some examples, the enzyme is conjugated to the antibody with a linker molecule (such as a maleimide linker) by reaction of a maleimido-enzyme molecule with a reduced antibody (such as an antibody having at least one free thiol, for example, at least 2, 3, 4, 5, 6, 7, 8, 9, 10, or more free thiols).

In particular embodiments described herein, the enzyme is AP. In some examples, the AP is a native AP (for example, intestinal AP, such as calf intestinal AP or kidney AP). Native AP can be purified using methods well known in the art and is also commercially available from many sources, including, but not limited to BioZyme (BBI Enzymes, Madison, Wis.), Sigma-Aldrich (St. Louis, Mo.), Worthington Biochemical (Lakewood, N.J.), and US Biological (Swampscott, Mass.). In other examples, the AP is a recombinant AP, such as a recombinant AP expressed in and purified from a microorganism (for example, *Escherichia coli* or *Pischia pastoris*). Methods for expressing and purifying recombinant AP are well known in the art. Recombinant AP is also commercially available, for example from Roche Applied Science (Indianapolis, Ind.), Worthington Biochemical (Lakewood, N.J.), and Sigma-Aldrich (St. Louis, Mo.). In a particular example, AP is modified with MAL-dPEG™$_{12}$ NHS (Quanta Biodesign; Powell, Ohio) to produce a maleimido-AP and an antibody (such as goat anti-mouse IgG or goat anti-rabbit IgG) is reduced with DTT to produce a thiolated antibody. The maleimido-AP and the thiolated antibody are reacted to produce an AP-antibody conjugate, which can be purified and used in the disclosed methods.

The disclosed methods include contacting the sample with an enzyme substrate and a metal ion, such that a metal precipitate forms. In particular examples, the sample is contacted with the enzyme substrate and the metal ion simultaneously. In other examples, the sample is contacted with the enzyme substrate and the metal ion sequentially. As discussed above, the enzymes utilized in the antibody-enzyme conjugate are those capable of transforming a redox-inactive enzyme substrate to produce at least one redox-active species capable of reducing metal ions to metal in a zero oxidation state. The enzyme substrate is therefore, a substrate that can be transformed by the particular enzyme included in the antibody-enzyme conjugate. In some examples, the enzyme is AP and the enzyme substrate is a molecule that includes a phosphate that can be removed by alkaline phosphatase, generating a redox-active species capable of reducing metal ions to metal in a zero oxidation state. Examples of AP substrates include, but are not limited to, indolyl phosphates (for example, 5-bromo-4-chloro-3-indolyl phosphate (BCIP)), ascorbic acid phosphate, α-tocopherol phosphate, sesamol phosphate, eugenol phosphate, and hydroquinone derivatives (for example, hydroquinone phosphate, naphthohydroquinone, and anthrahydroquinone). Additional AP substrates are known in the art (see, e.g., U.S. Pat. Nos. 7,632,652 and 7,642,064; incorporated herein by reference). In some examples, the sample is contacted with about 0.1 mM to about 100 mM enzyme substrate (such as about 0.4 mM to 75 mM, about 1 mM to 50 mM, or about 2 mM to 20 mM). In a particular example, the sample is contacted with about 0.5 to 3 mM BCIP, such as 1 to 2 mM BCIP, such as about 1.3 mM BCIP.

Similarly, for other enzymes, the substrate is a redox-inactive compound that can be transformed by the enzyme to at least one redox-active species capable of reducing metal ions to metal in a zero oxidation state. For example, if the enzyme is a β-galactosidase, the substrate can be a mono- or di-galactoside compound (for example, digalactosyl hydroquinone). If the enzyme is a β-lactamase, the substrate can be a β-lactam (such as a C3' β-lactam, for example, a cephalosporin). If the enzyme is a glucosidase, the substrate can be a mono- or di-glucoside and if the enzyme is an esterase, the substrate can be a mono- or di-ester. Particular examples of enzyme substrates appropriate for the methods described herein are known in the art (see, e.g., U.S. Pat. Nos. 7,632,652 and 7,642,064). One of skill in the art can determine substrates for a particular enzyme and select particular substrates that will produce the redox-active species.

As discussed above, the disclosed methods include an enzyme-antibody conjugate, wherein the enzyme transforms a substrate to a redox-active species capable of reducing metal ions to metal in a zero oxidation state. Without being bound by theory, it is believed that the reduced metal forms a precipitate that nucleates at the surface of the nanoparticle present in the sample in the form of the antibody-nanoparticle conjugate. This precipitate or deposit of metal atoms increases the size of the nanoparticle, which can then be detected, for example, using a light microscope. Metal ions suitable for the methods described herein include silver ions, gold ions, copper ions, nickel ions, platinum ions, palladium ions, cobalt ions, or iridium ions. In the methods described herein, the sample is contacted with a metal ion, which can be in a solution. In particular examples, a metal salt is dissolved in a solution. The metal salt can include a metal halide (such as a metal chloride or metal fluoride), a metal nitrate, a metal acetate, or a metal perchlorate. In other examples, the metal salt can include a metal sulfite, metal phosphate, or metal carbonate. In a particular example, the metal salt is silver nitrate.

In particular examples, the methods disclosed herein utilize an antibody-nanoparticle conjugate including gold nanoparticles and utilize silver ions, which are reduced to silver atom and deposited at the gold nanoparticle. In some examples, the silver ions are from silver compounds (for example, silver acetate, silver nitrate, silver fluoride, or silver perchlorate). In some examples, the sample is contacted with a solution including one or more silver compounds from about 10 mM to about 1 M (such as about 20 mM to 500 mM, or about 50 mM to 100 mM) for about 2 minutes to 90 minutes (such as about 2 minutes to 60 minutes, about 4 minutes to 60 minutes, or about 10 minutes to about 30 minutes). In a particular example, the sample is contacted with about 50 mM silver nitrate for about 20 minutes.

B. Antibody-Nanoparticle Conjugates

The methods described herein utilize an antibody conjugated to one or more nanoparticles (such as 1, 2, 3, 4, 5, 6, 7, 8, 9, 10, or more nanoparticles). In some examples, the antibody-nanoparticle conjugate is one described herein, wherein the antibody-nanoparticle conjugate includes two or more nanoparticles directly linked to the antibody through a metal-thiol bond. In a particular example, the antibody-nanoparticle conjugate is a conjugate including two to five gold nanoparticles per antibody, such as five gold nanoparticles. In other examples, the antibody-nanoparticle conjugate is any antibody-nanoparticle conjugate known to one of skill in the art. See, e.g., U.S. Pat. No. 5,360,895; U.S. Pat. Publication No. 2006/0246524.

As discussed above, in some examples, the nanoparticle is a metal nanoparticle (for example, gold, palladium, platinum, silver, copper, nickel, cobalt, iridium, or an alloy of two or more thereof). In some examples, the nanoparticle conjugated to the antibody has a diameter of about 0.5 nm to about 200 nm (for example, about 1 nm to about 100 nm, about 2 nm to about 50 nm, about 2 nm to about 10 nm, or about 1 nm to about 5 nm). In particular examples, the nanoparticles have a diameter of about 5 nm or less (such as about 5 nm, about 4.5 nm, about 4 nm, about 3.5 nm, about 3 nm, about 2.5 nm, about 2 nm, about 1.5 nm, about 1 nm, or about 0.5 nm). In some examples of the methods described herein, the sample is contacted with about 10 nM to 2 μM antibody-nanoparticle conjugate (such as about 20 nM to 1.5 μM, about 50 nM to 1 μM, or about 100 nM to 500 nM) for about 4 minutes to 60 minutes (such as about 8 minutes to 40 minutes, or about 16 minutes to 32 minutes). In a particular example, the sample is contacted with 100 nM of an antibody-gold nanoparticle conjugate for about 32 minutes.

C. Toning, Amplification, and Fixation

The methods disclosed herein optionally include a "toning" step that includes contacting the sample with a gold halide (such as gold chloride). Gold toning historically refers to treatment of a sample with gold chloride (with or without oxalic acid and thiosulfate) to protect a silver layer (for example for silver enhanced immunoelectron microscopy). See, e.g., Pohl and Stierhof, *Microsc. Res. Tech.* 42:59-65, 1998; Sawada and Esaki, *J. Histochem. Cytochem.* 48:493-498, 2000.

In particular examples of the disclosed methods, the sample is contacted with a gold halide (such as gold chloride) after the sample has been contacted with the enzyme substrate and the metal ion. See, e.g., U.S. Pat. Nos. 7,632,652 and 7,642,064, incorporated herein by reference. Without being bound by theory, it is believed that the gold is reduced and oxidizes some of the reduced metal atoms (such as silver) that are deposited at the surface of the nanoparticle of the antibody-nanoparticle conjugate (such as a gold nanoparticle), resulting in a darker spot (for example, increasing contrast and/or size of the signal). In some examples, the method includes contacting the sample with about 0.05% to about 1% (for example, about 0.1% to 0.8%, about 0.1% to 0.5%, or about 0.1% to 0.2%) gold chloride for about 2 minutes to about 90 minutes (such as about 2 minutes to 60 minutes, about 4 minutes to 60 minutes, or about 10 minutes to about 30 minutes). In a particular example, the sample is contacted with 0.2% gold chloride for about 4 minutes.

In some embodiments, the disclosed methods also optionally include an amplification step. The amplification can include contacting the sample with additional metal ions, providing more metal ions for reduction to metal in oxidation state zero and increasing the metal precipitate that can be detected. In some examples, the methods include contacting the sample with the same metal ion as that used in contacting the sample with the enzyme substrate and metal ion. In some examples, the metal ion is in the form of a metal salt dissolved in a solution. The metal salt can include a metal halide (such as a metal chloride or metal fluoride) or a metal nitrate. In a particular example, the metal ion is silver (for example, when the sample has been previously contacted with an enzyme substrate and silver ion), for example in the form of one or more silver compounds (for example, silver nitrate). In some examples, the sample is contacted with a solution including one or more silver compounds from about 10 mM to about 1 M (such as about 20 mM to 500 mM, or about 50 mM to 100 mM) for about 2 minutes to 90 minutes (such as about 2 minutes to 60 minutes, about 4 minutes to 60 minutes, or about 10 minutes to about 30 minutes). In a particular example, the sample is contacted with about 50 mM silver nitrate for about 4 minutes.

In additional embodiments, the methods disclosed herein optionally include a fixation step, which stops the metal reduction reaction and removes any unreduced metal ions from the sample. In some examples, the fixation includes contacting the sample with a reducing agent. In some examples, the methods include contacting the sample with about 0.01% to about 5% sodium thiosulfate (for example, about 0.0625% to 4%, about 0.1% to 3%, or about 0.5% to 2%) for about 2 minutes to 90 minutes (such as about 2 minutes to 60 minutes, about 4 minutes to 60 minutes, or about 10 minutes to about 30 minutes). In a particular example, the fixation includes contacting the sample with about 2% sodium thiosulfate for about 4 minutes.

V. Kits

Disclosed herein are kits, which can be used for carrying out various embodiments of the disclosed methods. In some examples, the kits include a first antibody conjugated to one or more nanoparticles (such as 1, 2, 3, 4, 5, 6, 7, 8, 9, 10, or more nanoparticles), such as the antibody-nanoparticle conjugates disclosed herein. In particular examples, the first antibody is conjugated to one or more gold nanoparticles, one or more palladium nanoparticles, one or more platinum nanoparticles, or one or more gold-palladium ally nanoparticles. In some examples, the kits also include a second antibody conjugated to one or more enzyme molecules (such as 1, 2, 3, 4, 5, 6, 7, 8, 9, 10, or more enzyme molecules) wherein the first antibody specifically binds to the second antibody. In some examples, the first antibody and/or the second antibody are anti-hapten antibodies. In some examples, the antibody conjugated to one or more nanoparticles is an antibody-nanoparticle conjugate disclosed herein, such as an antibody-nanoparticle conjugate including two or more nanoparticles (such as gold nanoparticles) directly linked to the antibody by a metal-thiol bond. In a specific example, the antibodies are included in separate containers.

In some specific examples, the kit includes a first antibody conjugated to one or more nanoparticles (such as 2, 3, 4, 5, 6, 7, 8, 9, 10, or more nanoparticles) and a second antibody conjugated to one or more AP molecules (such as 2, 3, 4, 5, 6, 7, 8, 9, 10, or more, for example, 3 AP molecules), where the first antibody specifically binds to the second antibody. In some examples, the second antibody is a "primary antibody" that specifically binds to a target molecule (such as a target protein or a hapten, where a hapten-labeled probe is bound to a target nucleic acid molecule). In other examples, the second antibody is a "secondary antibody" that specifically binds to a primary antibody (such as an antibody that specifically recognizes a target protein or a hapten, where a hapten-labeled probe is bound to a target nucleic acid molecule).

The kit optionally can include additional components, such as a substrate for the enzyme (for example, BCIP, if the enzyme is AP) or a solution including metal ions (such as a silver ions, gold ions, copper ions, nickel ions, platinum ions, palladium ions, cobalt ions, or iridium ions). Further, the kit can include additional components other then the above-identified reagents, including but not limited to reagents for additional steps of the disclosed methods, such as reagents for gold toning (for example, gold chloride), silver amplification (for example, silver nitrate), and/or fixation (for example, sodium thiosulfate). The kit can also include antibodies (such as one or more primary antibodies), hapten-labeled probes, or other reagents necessary for performing IHC and/or ISH by the methods disclosed herein. Each component of the disclosed kits can be provided in a separate container. In some examples, the kit may also include control samples, such as one or more positive control samples (for example, a sample known to express a particular target or to express a known amount or have a known gene copy number of a particular target) or one or more negative control samples (for example, a sample known not to express a particular target). In particular examples, the kits disclosed herein can be used to detect targets in samples from mammals that are suspected of having a disorder or disease, such as cancer or an infection.

VI. Samples and Targets

Samples include biological components and generally are suspected of including (or are even known to include) one or more target molecules of interest. Target molecules can be on the surface of cells and the cells can be in a suspension, or in a tissue section (e.g., a paraffin-embedded tissue section). Target molecules can also be intracellular and detected upon cell lysis or penetration of the cell by a probe or antibody. One of ordinary skill in the art will appreciate that the method of detecting target molecules in a sample will vary depending upon the type of sample and probe or antibody being used. Methods of collecting and preparing samples are known in the art.

Samples used in the methods described herein, such as a tissue or other biological sample can be prepared using any method known in the art. Samples include any solid or fluid sample obtained from, excreted by or secreted by any living organism, including without limitation, single celled organisms, such as bacteria, yeast, protozoans, and amoebas among others, multicellular organisms (such as plants or animals). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or a xenograft, or can include a cell (whether a primary cell or cultured cell) or medium conditioned by any cell, tissue or organ. In particular embodiments, the biological sample includes a tissue section (such as obtained by biopsy) or a cytology sample (such as a Pap smear or blood smear).

The samples can be obtained from subjects for routine screening or from subjects that are suspected of having a disorder, such as an infection, a genetic abnormality or a neoplasia. The described methods can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady.

The samples described herein can be prepared using any method now known or hereafter developed in the art. Generally, tissue samples are prepared by fixing and embedding the tissue in a medium. In other examples, samples include a cell suspension which is prepared as a monolayer on a solid support (such as a glass slide) for example by smearing or centrifuging cells onto the solid support. In further examples, fresh frozen (for example, unfixed) tissue sections may be used in the methods disclosed herein.

In some examples an embedding medium is used. An embedding medium is an inert material in which tissues and/or cells are embedded to help preserve them for future analysis. Embedding also enables tissue samples to be sliced into thin sections. Embedding media include paraffin, celloidin, OCT™ compound, agar, plastics, or acrylics.

Many embedding media are hydrophobic; therefore, the inert material may need to be removed prior to histological or cytological analysis, which utilizes primarily hydrophilic reagents. The term deparaffinization or dewaxing is broadly used herein to refer to the partial or complete removal of any type of embedding medium from a biological sample. For example, paraffin-embedded tissue sections are dewaxed by passage through organic solvents, such as toluene, xylene, limonene, or other suitable solvents.

The process of fixing a sample can vary. Fixing a tissue sample preserves cells and tissue constituents in as close to a life-like state as possible and allows them to undergo preparative procedures without significant change. Fixation arrests the autolysis and bacterial decomposition processes that begin upon cell death, and stabilizes the cellular and tissue constituents so that they withstand the subsequent stages of tissue processing, such as for IHC or ISH.

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing samples for IHC is formaldehyde, generally in the form of a formalin solution (4% formaldehyde in a buffer solution, referred to as 10% buffered formalin). In one example, the fixative is 10% neutral buffered formalin.

Samples can include multiple targets that can be specifically bound by a probe or antibody or reporter molecule. The targets can be nucleic acid molecules or proteins. Throughout this disclosure when reference is made to a target protein it is understood that the nucleic acid molecules associated with that protein can also be used as targets. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid molecule can vary substantially in size. Without limitation, the nucleic acid molecule can have a variable number of nucleic acid residues. For example a target nucleic acid molecule can have at least about 10 nucleic acid residues, or at least about 20, 30, 50, 100, 150, 500, 1000 or more residues. In some examples, the target nucleic acid molecule is a "short" nucleic acid molecule, such as about 1 kb to about 20 kb (for example, about 1 kb to about 15 kb, about 5 kb to about 20 kb, or about 5 kb to about 10 kb). In particular examples, "short" target nucleic acid molecules include viral genome sequences, such as HPV or Hepatitis virus. In other examples, the target nucleic acid molecule is a "long" nucleic acid molecule, such as about 20 kb to 500 kb (for example, about 20 kb to about 300 kb, about 50 kb to about 200 kb, or about 100 kb to about 200 kb) or more. In particular examples, "long" target nucleic acid molecules include genes associated with neoplastic transformation, such as EGFR, HER2, C-MYC, ABL, C-MET, TOP2A, BCL, p53, or RB1. The probe (such as a hapten-labeled probe) can bind to the target nucleic acid molecule and provide a detectable signal.

A target nucleic acid molecule can also vary substantially in copy number. Without limitation, the nucleic acid molecule can be present at a variable number of copies in a particular sample. For example a target nucleic acid molecule can be present in a sample at about 1 copy, or at least about 2, 3, 4, 5, 10, 20, 30, 50, 100, 150, 500, 1000 or more copies. In some examples, a target nucleic acid molecule is a "low copy number" nucleic acid, such as a nucleic acid that is present at about 1 to 100 copies per cell in the sample, such as about 1 to 50 copies, about 1 to 20 copies, about 1 to 10 copies, or about 1 to 3 copies. In particular examples, low copy number nucleic acid molecules include HER2 and HPV. In some examples, the target nucleic acid sequence is both a "short" nucleic acid sequence and a low copy number nucleic acid (such as HPV).

Similarly, a target protein or polypeptide can vary substantially in size. Without limitation, the target protein or polypeptide will include at least one epitope that binds to a probe or antibody. In some embodiments that protein or polypeptide can include at least two epitopes that bind to a probe or antibody. The probe or antibody can bind to the epitope and provide a detectable signal.

In specific, non-limiting examples, a target nucleic acid molecule or a target protein (such as a protein produced by a target nucleic acid (e.g., genomic target nucleic acid)) is associated with a neoplasm (for example, a cancer). Numerous chromosome abnormalities (including translocations and other rearrangements, reduplication or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is a nucleic acid molecule or a protein produced by a nucleic acid molecule (e.g., genomic target nucleic acid) that is reduplicated or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes nucleic acid molecules generated from a target nucleic acid sequence that extends distally from the SYT gene, and the second probe includes nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusion (generated by the two labels in close proximity) signals, reflecting the two intact copies of SYT. Abnormal cells with a t(18q11.2) exhibit a single fusion signal.

In other examples, a target nucleic acid or a target protein (such as a protein produced by a target nucleic acid (e.g., genomic target nucleic acid)) is selected that is a tumor suppressor gene that is deleted (lost) in malignant cells. For example, the p16 region (including D9S1749, D9S1747, p16 (INK4A), p14 (ARF), D9S1748, p15 (INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target nucleic acids or target proteins (such as a protein produced by a target nucleic acid (e.g., genomic target nucleic acid)) which have been correlated with neoplastic transformation and which are useful in the disclosed methods, also include the EGFR gene (7p12; e.g., GENBANK™ Accession No. NC_000007, nucleotides 55054219-55242525), the C-MYC gene (8q24.21; e.g., GENBANK™ Accession No. NC_000008, nucleotides 128817498-128822856), D5S271 (5p15.2), lipoprotein lipase (LPL) gene (8p22; e.g., GENBANK™ Accession No. NC_000008, nucleotides 19841058-19869049), RB1 (13q14; e.g., GENBANK™ Accession No. NC_000013, nucleotides 47775912-47954023), p53 (17p13.1; e.g., GENBANK™ Accession No. NC_000017, complement, nucleotides 7512464-7531642)), N-MYC (2p24; e.g., GENBANK™ Accession No. NC_000002, complement, nucleotides 151835231-151854620), CHOP (12q13; e.g., GENBANK™ Accession No. NC_000012, complement, nucleotides 56196638-56200567), FUS (16p11.2; e.g., GENBANK™ Accession No. NC_000016, nucleotides 31098954-31110601), FKHR (13p14; e.g., GENBANK™ Accession No. NC_000013, complement, nucleotides 40027817-40138734), as well as, for example: ALK (2p23; e.g., GENBANK™ Accession No. NC_000002, complement, nucleotides 29269144-29997936), Ig heavy chain, CCND1 (11q13; e.g., GENBANK™ Accession No. NC_000011, nucleotides 69165054-69178423), BCL2 (18q21.3; e.g., GENBANK™ Accession No. NC_000018, complement, nucleotides 58941559-59137593), BCL6 (3q27; e.g., GENBANK™ Accession No. NC_000003, complement, nucleotides 188921859-188946169), MALF1, AP1 (1p32-p31; e.g., GENBANK™ Accession No. NC_000001, complement, nucleotides 59019051-59022373), TOP2A (17q21-q22; e.g., GENBANK™ Accession No. NC_000017, complement, nucleotides 35798321-35827695), TMPRSS (21q22.3; e.g., GENBANK™ Accession No. NC_000021, complement, nucleotides 41758351-41801948), ERG (21q22.3; e.g., GENBANK™ Accession No. NC_000021, complement, nucleotides 38675671-38955488); ETV1 (7p21.3; e.g., GENBANK™ Accession No. NC_000007, complement, nucleotides 13897379-13995289), EWS (22q12.2; e.g., GENBANK™ Accession No. NC_000022, nucleotides 27994271-28026505); FLI1 (11q24.1-q24.3; e.g., GENBANK™ Accession No. NC_000011, nucleotides 128069199-128187521), PAX3 (2q35-q37; e.g., GENBANK™ Accession No. NC_000002, complement, nucleotides 222772851-222871944), PAX7 (1p36.2-p36.12; e.g., GENBANK™ Accession No. NC_000001, nucleotides 18830087-18935219, PTEN (10q23.3; e.g., GENBANK™ Accession No. NC_000010, nucleotides 89613175-89716382), AKT2 (19q13.1-q13.2; e.g., GENBANK™ Accession No. NC_000019, complement, nucleotides 45431556-45483036), MYCL1 (1p34.2; e.g., GENBANK™ Accession No. NC_000001, complement, nucleotides 40133685-40140274), REL (2p13-p12; e.g., GENBANK™ Accession No. NC_000002, nucleotides 60962256-61003682) and CSF1R (5q33-q35; e.g., GENBANK™ Accession No. NC_000005, complement, nucleotides 149413051-149473128).

In other examples, a target nucleic acid or target protein is selected from a virus or other microorganism associated with a disease or condition. Detection of the virus- or microorganism-derived target nucleic acid (e.g., genomic target nucleic acid) or target protein in a cell or tissue sample is indicative of the presence of the organism. For example, the target nucleic acid, peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum*, *Entamoeba histolytica*, and *Giardia lamblia*, as well as *Toxoplasma, Eimeria, Theileria*, and *Babesia* species).

In some examples, the target nucleic acid or target protein (such as a protein produced by a target nucleic acid (e.g., genomic target nucleic acid)) is from a viral genome. Exemplary viruses and corresponding genomic sequences (GENBANK™ RefSeq Accession No. in parentheses) include human adenovirus A (NC_001460), human adenovirus B (NC_004001), human adenovirus C (NC_001405), human adenovirus D (NC_002067), human adenovirus E (NC_003266), human adenovirus F (NC_001454), human astrovirus (NC_001943), human BK polyomavirus (V01109; GI:60851) human bocavirus (NC_007455), human coronavirus 229E (NC_002645), human coronavirus HKU1 (NC_006577), human coronavirus NL63 (NC_005831), human coronavirus OC43 (NC_005147), human enterovirus A (NC_001612), human enterovirus B (NC_001472), human enterovirus C (NC_001428), human enterovirus D (NC_001430), human erythrovirus V9 (NC_004295), human foamy virus (NC_001736), human herpesvirus 1 (Herpes simplex virus type 1) (NC_001806), human herpesvirus 2 (Herpes simplex virus type 2) (NC_001798), human herpesvirus 3 (Varicella zoster virus) (NC_001348), human herpesvirus 4 type 1 (Epstein-Barr virus type 1) (NC_007605), human herpesvirus 4 type 2 (Epstein-Barr virus type 2) (NC_009334), human herpesvirus 5 strain AD169 (NC_001347), human herpesvirus 5 strain Merlin Strain (NC_006273), human herpesvirus 6A (NC_001664), human herpesvirus 6B (NC_000898), human herpesvirus 7 (NC_001716), human herpesvirus 8 type M (NC_003409), human herpesvirus 8 type P (NC_009333), human immunodeficiency virus 1 (NC_001802), human immunodeficiency virus 2 (NC_001722), human metapneumovirus (NC_004148), human papillomavirus-1 (NC_001356), human papillomavirus-18 (NC_001357), human papillomavirus-2 (NC_001352), human papillomavirus-54 (NC_001676), human papillomavirus-61 (NC_001694), human papillomavirus-cand90 (NC_004104), human papillomavirus RTRX7 (NC_004761), human papillomavirus type 10 (NC_001576), human papillomavirus type 101 (NC_008189), human papillomavirus type 103 (NC_008188), human papillomavirus type 107 (NC_009239), human papillomavirus type 16 (NC_001526), human papillomavirus type 24 (NC_001683), human papillomavirus type 26 (NC_001583), human papillomavirus type 32 (NC_001586), human papillomavirus type 34 (NC_001587), human papillomavirus type 4 (NC_001457), human papillomavirus type 41 (NC_001354), human papillomavirus type 48 (NC_001690), human papillomavirus type 49 (NC_001591), human papillomavirus type 5 (NC_001531), human papillomavirus type 50 (NC_001691), human papillomavirus type 53 (NC_001593), human papillomavirus type 60 (NC_001693), human papillomavirus type 63 (NC_001458), human papillomavirus type 6b (NC_001355), human papillomavirus type 7 (NC_001595), human papillomavirus type 71 (NC_002644), human papillomavirus type 9 (NC_001596), human papillomavirus type 92 (NC_004500), human papillomavirus type 96 (NC_005134), human parainfluenza virus 1 (NC_003461), human parainfluenza virus 2 (NC_003443), human parainfluenza virus 3 (NC_001796), human parechovirus (NC_001897), human parvovirus 4 (NC_007018), human parvovirus B19 (NC_000883), human respiratory syncytial virus (NC_001781), human rhinovirus A (NC_001617), human rhinovirus B (NC_001490), human spumaretrovirus (NC_001795), human T-lymphotropic virus 1 (NC_001436), human T-lymphotropic virus 2 (NC_001488).

In certain examples, the target nucleic acid or target protein (such as a protein produced by a target nucleic acid (e.g., genomic target nucleic acid)) is from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

The disclosure is further illustrated by the following non-limiting Examples.

EXAMPLES

Example 1

Synthesis of a Gold Nanoparticle-Antibody Conjugate AuNP Synthesis $N_2$ sparged water (30 ml) was placed in a 500 ml round bottom flask equipped with a large oval stir bar and nitrogen. Then 0.5 g (1.27 mmol) of $HAuCl_4$ was added to the reaction flask and stirred until all the salt was solubilized. Next 30 ml of $N_2$ sparged toluene was added; followed by 0.700 grams of the phase transfer agent, tetraoctylammonium bromide (TOABr). The mixture was stirred until the auric acid was transferred from the aqueous phase to the organic phase. Once the phase transfer of the auric acid was complete, 1.15 g of triphenylphosphine (TPP) was added and stirred vigorously until a white suspension appeared, at which point stirring continued for 10-15 minutes. All stirring was done at a speed that mixed aqueous and organic layers.

In a separate container, 0.72 g of $NaBH_4$ in 5 ml of water was prepared and gently stirred until all the reducing agent was dissolved. The $NaBH_4$ solution was quickly added to the reaction flask with rapid stirring for 3 hours. The system was septa closed with a bubbler to vent gas produced in this reaction.

At the end of the reaction, the reaction mixture was transferred to a separatory funnel and the aqueous layer was removed. The organic layer was washed three times with 100 ml of water or until the aqueous layer was clear. If an emulsion formed, brine or trisodium citrate was added to break it up.

The toluene was evaporated under reduced pressure (rotary evaporator) until a black solid remained. The material was resuspended in hexanes (breaking apart large aggregates) and transferred to a 250 to 500 ml fine or medium sintered glass frit on a vacuum Erlenmeyer flask. The hexanes were filtered away from the precipitate and washed with three times with 100 ml of hexanes. The precipitate was then washed five times with 100 ml of 2:1 water:methanol, five times with 100 ml of water, five times with 100 ml of 3:2 water:methanol, and then five times with 100 ml of water. A final wash of five portions of 100 ml of hexanes was done. For further purification, the solids were transferred to a flask and re-solvated in 20 ml of dichloromethane. This was sonicated for 5 min and then hexanes were slowly added until the solution become turbid. The solution was transferred to centrifuge tubes and the solids were collected at 2500 rpm. This solvation and precipitation was done another time to further purify the material, if necessary.

UV-Vis absorption spectrum was measured from 250-750 nm. Absorbance at 520 nm was inspected to determine if there was pre-SPR band. This indicated a nanoparticle at about 1.5 nm to 2 nm. Absorbance at 460 nm was measured to determine concentration and amount of sample in solution using the extinction coefficient of 64,000 $(cm^{-1})(M^{-1})$.

AuNP Conversion to Water-Soluble Nanoparticles

AuNPs (50 mg) were added to a 250 ml round bottom flask equipped with a large oval stir bar and nitrogen line. Then 20 ml of dichloromethane was added and stirred until the AuNPs were in solution. Next 30 ml of $N_2$ sparged water was added to the reaction flask, followed by 50 mg of bis-(sulfonatophenyl)phenylphosphine (BSPP); the reaction was stirred vigorously for at least 24 hours. If the material was not completely transferred to the aqueous phase, an additional 50 mg of BSPP was added and stirred for another 24 hours.

After the material was delivered to the aqueous phase, the contents of the reaction were transferred to a separatory funnel and the organic layer was removed. The aqueous phase was washed with 20 ml of dichloromethane and then filtered through a 0.2 pm filter. The water was removed under reduced pressure and the nanomaterial was stored at −20° C.

AuNP Conjugation to Rabbit Anti-Goat IgG

The AuNP material was removed from the freezer and brought to room temperature. 5 mg was placed into a 2 ml Eppendorf® tube and resuspended in 1 ml of 20 mM phosphate buffer (PB), pH 7.4. The material was sonicated for 2-3 min and gently filtered through a 0.2 μm syringe filter remove large aggregates. The eluted solution was passed through a PD-10 size exclusion-desalting column (equilibrated with 20 mM PB pH 7.4) to remove small molecules and salts.

A dithiothreitol (DTT) solution was prepared by adding 7.7 mg of DTT to 100 μl of water. Then 1.5 mg rabbit anti-goat antibody was placed in a 2 ml Eppendorf® tube and 43.8 μl of the DTT solution was added and mixed at 4° C. for 25 minutes The reduced protein was separated from the excess DTT solution using a PD-10 size exclusion-desalting column (equilibrated with 20 mM PB pH 7.4). Ten 500 μl fractions were collected and each fraction was measured by UV-Vis absorption at 280 nm for protein content. The fractions containing protein were pooled and added to the AuNP solution. The solution was gently mixed at 4° C. for 48 hours.

Figure 2B:
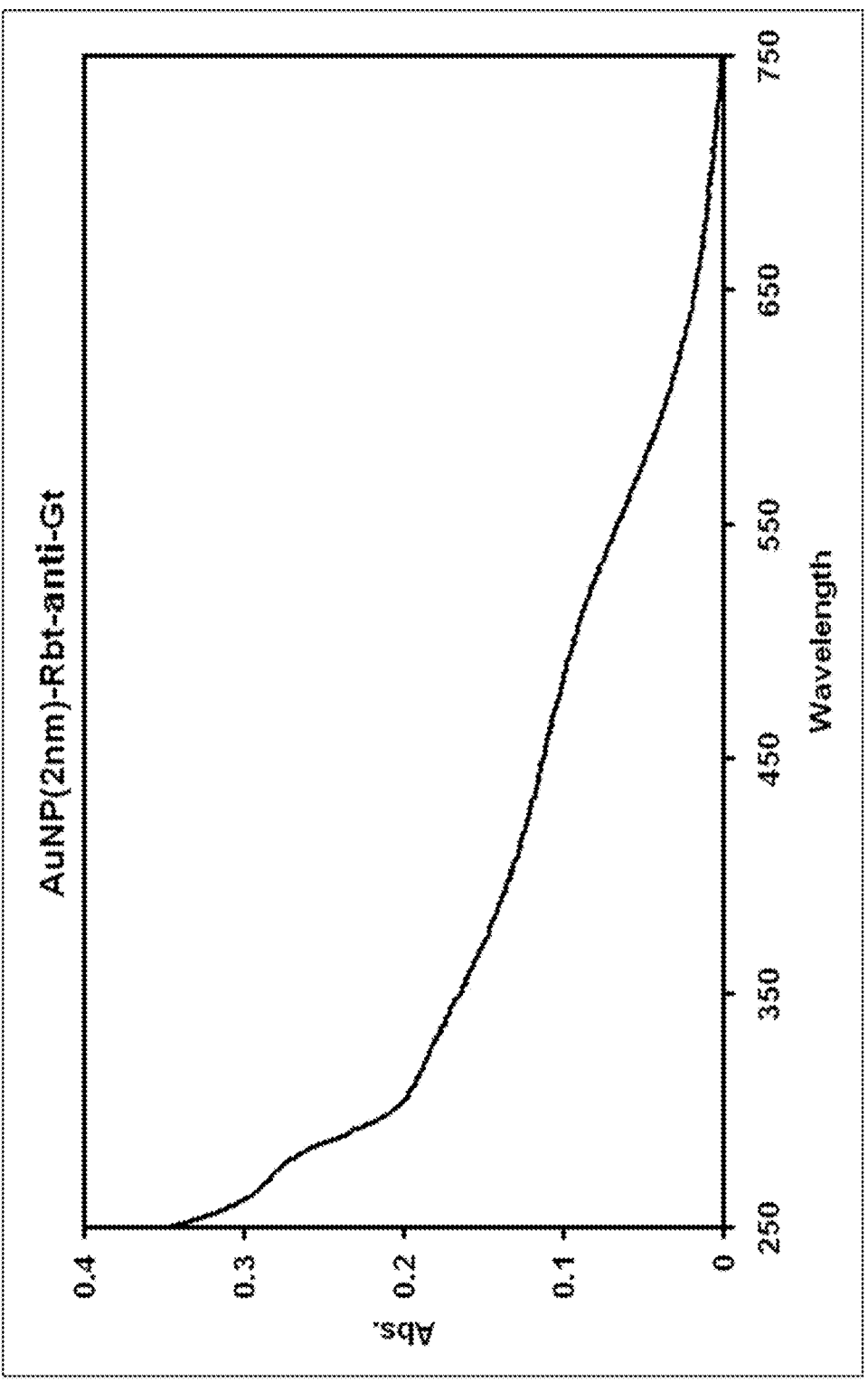
FIG. 2B is a UV-Vis absorption trace of the purified AuNP-antibody conjugate shown in FIG. 2A.

A pre-purification step of gently filtering the conjugation reaction through a 0.2 μm syringe filter was done before the final purification which was done on an AKTA SEC purifier using a GE Superdex® 200 column using 20 mM PB pH 7.4. The chromatogram was set to measure absorbance at 280 nm and 460 nm and 500 fractions were collected. Fractions under the major peak were collected (FIG. 2A). After the fractions were pooled, a final filtration through a 0.2 μm syringe filter was done for a final purification step. UV-Vis absorption was done to characterize the material at 280 nm and 460 nm to quantitate the protein and AuNP ratios and final conjugate concentrations (FIG. 2B). The resulting antibody-nanoparticle conjugate included about 3.5 nanoparticles per antibody.

Example 2

Synthesis of Additional Nanoparticle-Antibody Conjugates

Platinum nanoparticles (PtNP) were synthesized as described in Example 1 for AuNPs, except the $HAuCl_4$ was replaced with potassium tetrachloroplatinate. Palladium nanoparticles (PdNP) were also synthesized as described in Example 1 for AuNPs, except the $HAuCl_4$ was replaced with sodium tetrachloropalladate. Finally, gold-palladium alloy nanoparticles (AuPdNP) were synthesized as described in Example 1 for AuNPs, except the $HAuCl_4$ was replaced with 0.25 g (0.64 mmol) of $HAuCl_4$ and 0.19 g (0.64 mmol) of $Na_2PdCl_4$. Purification, ligand exchange, and conjugation to antibody for each was as described in Example 1.

Example 3

Synthesis and Characterization of Alkaline Phosphatase-Antibody Conjugates

An AP-antibody conjugate was produced by reacting maleimido-AP with a reduced antibody. The number of AP molecules per enzyme was varied by adjusting the ratio of AP to antibody in the reaction.

AP (BBI Enzymes, Madison, Wis.) was buffer exchanged through an equilibrated PD-10 column with AP buffer 1 (0.1 M $Na_3PO_4$, 0.1 M NaCl, 1 mM $MgCl_2$, 0.1 mM $ZnCl_2$, pH 7.5) to remove Tris buffer. The AP was then activated for conjugation by treatment with 50-100-fold molar excess of MAL-dPEG™$_{12}$ NHS ester (1-maleinimido-3-oxo-7,10,13,16,19,22,25,28,31,34,37,40-dodecaoxa-4-azatritetracontan-43-oic acid succinimidyl ester; Quanta Biodesign, Powell, Ohio) at ambient temperature (23-25° C.) for 60 minutes. Size exclusion chromatography (SEC) using a Superdex® 200 10/300 GL column equilibrated with AP buffer 2 (0.1 M Tris-HCl, 1 mM $MgCl_2$, 0.1 mM $ZnCl_2$, pH 7.5) yielded the purified maleimido-AP.

Anti-mouse IgG, anti-rabbit IgG, mouse anti-benzofurazan, or mouse anti-DNP antibody was incubated with 25 mM DTT at ambient temperature (23-25° C.) for 25 minutes. After purification across a PD-10 desalting column (0.1 M NaOAc, pH 5. 0), DTT-free antibody with four to eight free thiols was obtained.

The purified thiolated antibody was combined with the purified maleimido-AP at a three-fold molar excess of the maleimido-AP. The mixture was incubated at ambient temperature (23-25° C.) for 16-18 hours. SEC using a Superdex® 200 10/300 GL column equilibrated with AP buffer 2 yielded the purified AP-antibody conjugate.

To examine the types of conjugates formed, AP-IgG conjugates were synthesized with different stoichiometries. Ratios of 1 IgG:1 AP to 1 IgG:5 AP were utilized in the synthesis. The 1 IgG: 1 AP conjugate aggregated completely; a precipitate was observed. When the supernatant was analyzed by SEC, a peak was observed corresponding to large sized materials unresolved by the column. The 1 IgG:2 AP and 1 IgG:3 AP gave some aggregated materials, but showed a second peak when isolated and performed exceptionally well in tissue staining These conjugates performed equal to or better than a control AP conjugate which is a 1 IgG:1 AP ratio (Ventana Medical Systems, Part No. 253-4327). The 1 IgG:3 AP to 1 IgG:5 AP exhibited more unreacted alkaline phosphatase and performed equivalently to the 1 IgG: 2 AP conjugate when tested on tissue.

In addition to the variation of stoichiometries between AP and IgG, conjugates were synthesized with a different stoichiometry between AP and MAL-dPEG™₁₂ NHS ester (Mal). Once reacted with the reduced IgG, the reactions were examined by SEC. IgG:3 AP 50× and 100× Mal reactions provided better resolution and yield with less free AP-Mal starting material. Other ratios showed increased levels of aggregation and unreacted AP-Mal complexes. On functional tissue staining, the IgG:3 AP 50× and 100× Mal conjugates performed better than the 200× and 400× excess Mal.

The hydrodynamic size of the IgG-AP conjugates was analyzed by dynamic light scattering. The size distribution of the conjugates is shown in Table 1. This shows that the IgG-AP conjugate made with a 1:3 stoichiometry is larger and contains more AP than the control AP conjugate.

TABLE 1

Dynamic light scattering analysis of IgG-AP conjugates

| Sample | Size |
|---|---|
| Goat anti-rabbit antibody | 9.6 nm |
| Alkaline phosphatase | 7.6 nm |
| Control IgG-AP conjugate (1 IgG:1 AP) | 15.95 nm |
| Goat anti-rabbit:3 AP (not diluted) | 21.73 nm |
| Goat anti-rabbit:3 AP (diluted to concentration of control conjugate) | 17.09 nm |

A comparative enzyme activity assay was performed with three different IgG-AP conjugates (two different batches of IgG:3 AP and one batch of IgG:2 AP) and the control IgG-AP conjugate (1 IgG:1 AP). Enzyme activity was measured at 405 nm using a Beckman DU-530 UV/VIS spectrophotometer, with 4-nitrophenylphopshate as the substrate (see, e.g., ThermoScientific Cat. No. TR11103). The IgG:3 AP conjugate had 2.3 times more enzyme activity than the control conjugate. The IgG:2 AP conjugate had higher activity than the control conjugate, but only half that of IgG:3 AP (Table 2). The two IgG:3 AP batches performed equivalently.

TABLE 2

Enzyme activity assay

| Sample | Enzyme activity (U/ml) |
|---|---|
| Control IgG-AP conjugate (1 IgG:1 AP) | 4464 |
| Goat anti-rabbit:3 AP (batch 1) | 10,414 |
| Goat anti-rabbit:3 AP (batch 2) | 10,354 |
| Goat anti-rabbit:2 AP | 5908 |

The performance of native bovine intestinal AP was compared with recombinant AP produced in *Pischia pastoris* (Roche Diagnostics, Cat. No. 03 359 123 001). The recombinant AP had fewer isoenzymes and slightly different N-glycosylation compared to the native AP. Both native and recombinant AP were treated with MAL-dPEG™₁₂NHS linker and purified by SEC. The chromatograms showed similar retention and elution profiles. The linker-modified APs were then coupled to DTT reduced goat anti-rabbit IgG. The AP-antibody conjugates were purified by SEC and elution profiles of both the native and recombinant conjugates were similar. Additional evaluation of the recombinant AP-antibody conjugate by ISH and IHC staining demonstrated similar signal intensity and specificity compared to the native AP-antibody conjugate. This demonstrates that recombinant AP can be used as an alternative to conventional, native AP.

The IgG-AP conjugates were analyzed by native and reducing SDS-PAGE. Control IgG-AP conjugate migrated as two major bands (about 290 kDa and 530 kDa) on a Novex 4-16% Bis-Tris gel (Invitrogen, Cat. No. BN2111BX10), while the IgG-AP conjugates made as described above migrated more slowly with at least two major band (about 450 kDa and 570 kDa) and a minor band at about 500 kDa (FIG. 3A). The electrophoretic profiles of the conjugates synthesized with different molar excess of the MAL-dPEG™₁₂NHS ester were similar. The conjugate synthesized with a 2 molar excess of AP appeared to have aggregated in solution, unlike the conjugates which were synthesized with a 3 molar excess of AP (FIG. 3A). This was consistent with the SEC data (above).

The conjugates were also analyzed on a NuPAGE Novex 3-8% Tris-acetate SDS reducing gel. Similar to the native PAGE results, the control IgG-AP conjugate migrated faster than the new AP conjugates. The IgG-AP conjugates synthesized by the current methods were represented by three major bands with molecular weights ranging from about 430 to 710 kDa, consistent with the conjugation stoichiometry of 1 IgG:2 AP (about 430 kDa), 1 IgG:3 AP (about 570 kDa), and 1 IgG:4 AP (about 710 kDa) (FIG. 3B). The electrophoretic profiles of the conjugates synthesized with varying molar excess of the MAL-dPEG™₁₂NHS ester were similar. The conjugate synthesized with recombinant AP was represented by one major band at about 710 kDa. This difference may be due to the different mannose branching pattern of the recombinant AP, which may facilitate the conjugation of more AP molecules per antibody and/or create a very stable secondary structure.

The number of AP molecules per antibody in the AP-antibody conjugate was determined by labeling the antibody with a fluorescent marker. Goat anti-rabbit IgG in 20 mM phosphate buffer (pH 7.4) was combined with Alexa Fluor® 610 NHS-ester (Life Technologies/Invitrogen, Carlsbad, Calif.) in DMSO and rotated for 12-15 hours at ambient temperature. The resulting conjugate was purified using a Superdex® 200 10/300 GL size exclusion column that was equilibrated with 20 mM phosphate buffer (pH 7.4). The product was serially diluted in phosphate buffer and UV readings were taken at 280 and 610 nm. The number of Alexa Fluor® 610 molecules per antibody was calculated. Synthesis of goat anti-rabbit Alexa Fluor® conjugates was performed twice; the average number of AP per antibody was calculated to be 3.15.

Conjugation of the fluorescently labeled antibody to AP was performed as described above, using a ratio of antibody: AP of 1:2 or 1:3. Conjugates were purified using a Superdex® 200 10/300 GL column and the number of AP per antibody was calculated. The conjugate synthesized with a 1:2 ratio of antibody:AP had 1.67 AP per antibody. The conjugate synthesized with a 1:3 ratio of antibody:AP had 2.6 AP per antibody. This confirms that multiple AP molecules can be conjugated to an antibody and that the number can be adjusted by changing the stoichiometry of the reactants.

Example 4

In Situ Hybridization Using Antibody-Gold Nanoparticle Conjugates

An assessment of the novel AP-silver detection kit versus an HRP detection system was performed using a chromosome 17 probe on xenograft cell lines. Slide staining was performed on an automated BenchMark® XT Instrument (Ventana Medical Systems, Inc. (VMSI)) using HER2 3-in-1 xenograft slides (VMSI #783-4332). Briefly, formalin-fixed paraffin embedded (FFPE) tissue slides were heated to 75° C. for 4 min, treated twice with EZPrep™ (10×, VMSI #950-102) and coverslipped by application of liquid coverslip (VMSI #650-010). Following coverslipping, the tissue slides were heated to 76° C. for 4 minutes, rinsed with EZPrep™, and liquid coverslip was reapplied for tissue deparaffinization. The slide was cooled to 37° C., incubated for 4 minutes, and rinsed with Reaction Buffer (10×, VMSI #950-300).

Once rinsed with Reaction Buffer, the tissue slides were heated to 95° C. and pretreated with Cell Conditioning Solution #1 (CC1, VMSI #950-124) for the cycles of 8, 12 and 8 minutes, wherein liquid coverslip was applied between each CC1/cycle application. After cycling with CC1, the slides were heated to 37° C., incubated for 4 minutes and rinsed once with Reaction Buffer. The tissue samples were protease treated by application of ISH-Protease 3 (VMSI #780-4149) for 4 minutes, rinsed with Reaction Buffer to remove the protease, and finally rinsed with SSC (10×, VMSI #950-110).

Silver in situ hybridization detection solution (VMSI, ultraView™ SISH Detection Kit #780-001) was added to the protease treated tissue slides, the slides were incubated for 4 minutes, and HER2 DNP Labeled DNA Probe (VMSI #780-4332) or Chromosome 17 (Chr17) Probe (VMSI #780-4331) was applied to the appropriate slide. Following probe application, the slides were incubated for 4 minutes, followed by nucleic acid denaturation at 95° C. for 12 minutes. Liquid coverslip was subsequently applied on the slides and hybridization was allowed to occur for 2 hours at 52° C. (HER2 probe) or 44° C. for 2 hours (Chr17 probe).

Following hybridization, the slides were rinsed in SSC, washed three times at 72° C. for 8 minutes each using 2×SSC, at which point the slide heating ceased and the slides were allowed to cool. Once cooled, the slides were rinsed in Reaction Buffer and warmed to 37° C. for 4 min, after which Rabbit anti-DNP (VMSI #780-4335) was applied, the slides were coverslipped with liquid coverslip, and incubated at 37° C. for 20 minutes. Following incubation, the slides were rinsed twice with Reaction Buffer, 15 µg/ml Goat anti-Rabbit recombinant Alkaline Phosphatase conjugate (Example 3) was applied and the slides were incubated another 32 minutes at 37° C. After incubation, the slides were washed four times with Reaction Buffer. Then 100 nM Rabbit anti-Goat gold nanoparticle conjugate (Example 1) was applied and the slides were incubated at 37° C. for an additional 32 minutes prior to washing three times with 0.1 M Tris acetate buffer at pH 9.0.

To detect the probe/target hybridization events, 50 mM silver nitrate and 1.3 mM BCIP were added to the slides and the slides were incubated at 37° C. for 20 minutes after coverslipping with liquid coverslip. Gold toning was performed by rinsing the slides twice in Tris Buffer, application of approximately 100 µl of 0.2% gold chloride solution, coverslipping, and incubation of the slides for 4 minutes at 37° C. The slides were rinsed twice in Tris buffer, silver nitrate was reapplied, liquid coverslip was applied, and the slides were incubated for an additional 4 minutes to effect signal amplification. After an additional Tris buffer wash the detection signal deposition was fixed by the application sodium thiosulfate to the slides. Following a 4 minutes incubation with sodium thiosulfate, the slides were rinsed in Reaction Buffer and counterstained by the application and incubation of Hematoxylin II (VMSI #790-2208) and liquid coverslip for 4 minutes. Bluing Reagent (VMSI #760-2037) was added after the Hematoxylin II/liquid coverslip was washed off the slides and after an additional 4 minutes incubation the counterstaining was completed.

Once the staining and counterstaining was complete, the slides were removed from the instrument, detergent washed, dehydrated through a graduated series of alcohol and xylene solutions, a solid coverslip was applied to the slip, and the slides were finally viewed through a brightfield microscope.

Figure 4:
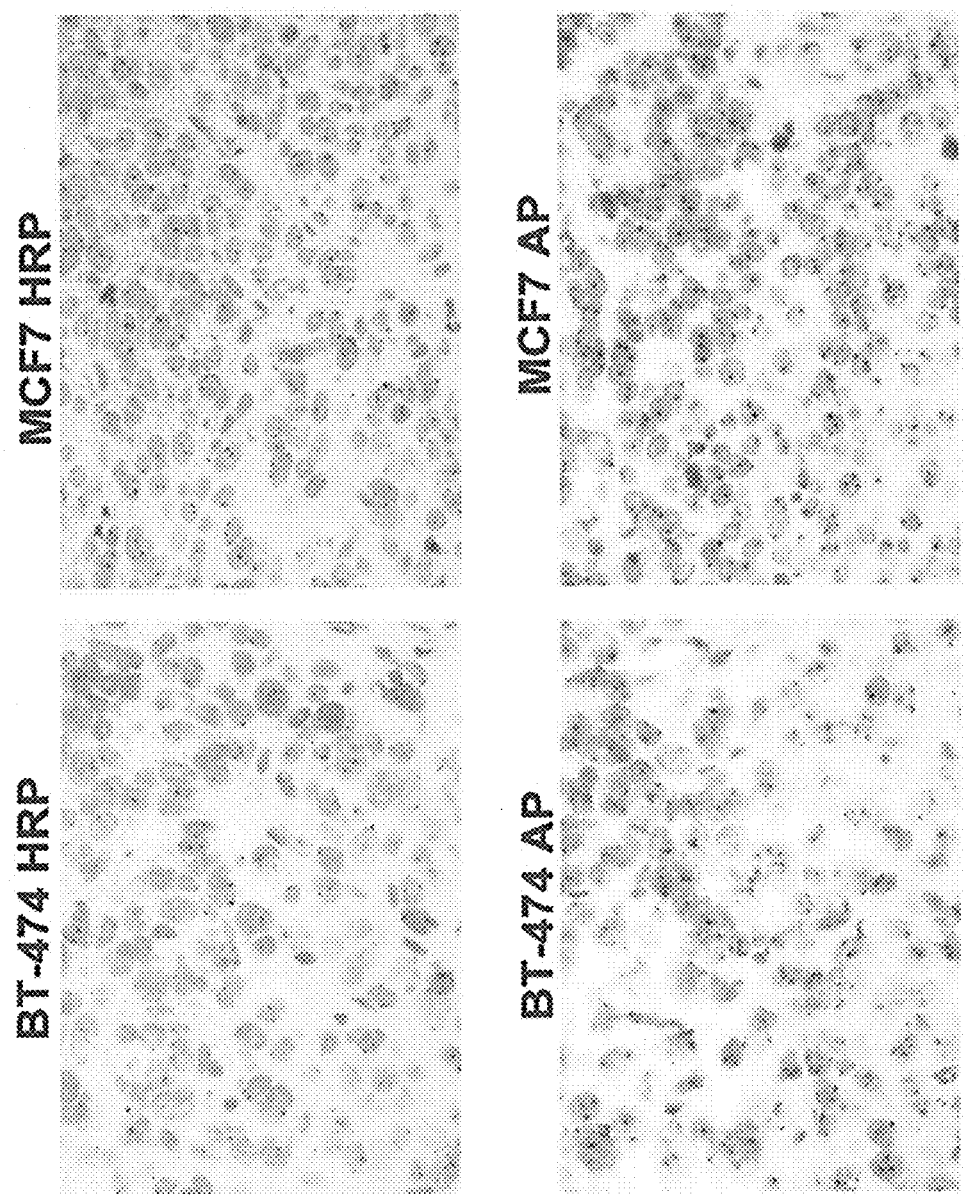
FIG. 4 is a series of digital images of ISH of breast tumor cell line xenografts (BT-474 and MCF7 cells) using a Chromosome 17 probe. The probe was detected by standard HRP SISH (top panels) or the disclosed AP silver detection method utilizing antibody-gold nanoparticle conjugate (bottom panels).
Figure 5:
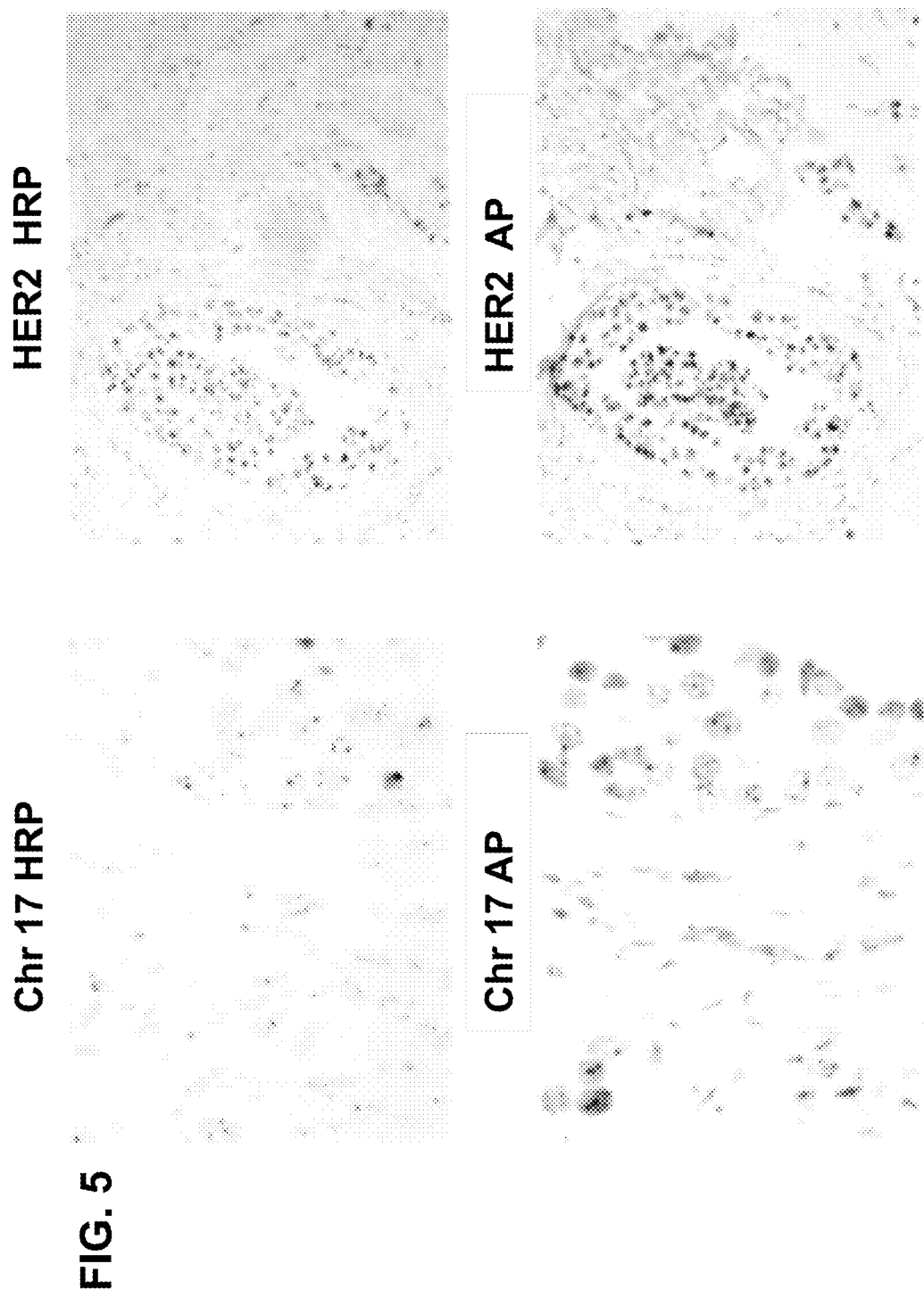
FIG. 5 is a series of digital images of ISH of breast carcinoma tissue with a Chromosome 17 probe (left) and a HER2 probe (right). The probes were detected by standard HRP SISH (top panels) or the disclosed AP silver detection method utilizing antibody-gold nanoparticle conjugate (bottom panels).

The stained slides were judged on background/non-specific staining, signal intensity, and sensitivity. In both cases, the silver detection utilizing the antibody-gold nanoparticle conjugate synthesized as in Example 1 and the IgG-AP conjugate synthesized as in Example 3 exhibited greater signal intensity with equal levels of background as the conventional HRP detection system (FIG. 4). The two systems were also compared using breast carcinoma tissue with chromosome 17 and HER2 probes. In the case of the chromosome 17 probe, similar high quality of detection, signal intensity, and clarity was observed in the breast carcinoma as in the xenografts. For the HER2 probe, the new method outperformed the conventional HRP detection system with a higher number of cells detected and greater signal intensity with no appreciable background (FIG. 5).

To determine the effect of the antibody-nanoparticle conjugate on tissue staining, Calu xenografts were stained for HER2 ribonucleic acid probe with and without the antibody-nanoparticle conjugate in an AP SISH system. Slide staining was performed on an automated BenchMark® XT Instrument. Briefly, slides containing FFPE Calu-3 tissue were heated to 75° C. for 4 min, treated twice with EZPrep™, and coverslipped by application of liquid coverslip. Following coverslipping, the tissue slides were incubated at 75° C. for 16 minutes, rinsed with EZPrep™, and liquid coverslip was reapplied for tissue deparaffinization. Slides were cooled to 37° C., incubated for 4 minutes, and rinsed with SSC. One drop (approximately 100 µl) of RiboPrep™ Reagent (VMSI, RiboMap® Kit #760-102) was applied to the slides, liquid coverslip was applied, and the slides were incubated for 32 minutes at 37° C. Following incubation, the slides were rinsed in EZPrep™ RiboClear™ (approximately 100 µl, a component of RiboMap® Kit) was applied, and the slides were incubated an additional 12 minutes at 37° C. after application of liquid coverslip.

Reaction Buffer was used to rinse the slides twice, liquid coverslip was reapplied, and the slides were incubated at 90° C. for 8 minutes, after which time the slides were rinsed and ISH-Protease 3 was applied after the temperature was cooled to 37° C. and the slides were incubated for 4 minutes. Following protease digestion, the slides were rinsed three times with Reaction Buffer, 100 µl of HER2 DNP Labeled RNA Probe was applied to the slides in conjunction with SISH detection hybridization solution, the slides were incubated for 12 minutes at 80° C., and liquid coverslip was applied and hybridization was allowed to proceed for 6 hours at 65° C. After hybridization, the slides were rinsed with EZPrep™ and three stringent washes of 0.1×SSC at 8 minutes per wash were performed at 75° C. Following the washes, the slides were rinsed in EZPrep™ and approximately 100 µl of RiboFix™ (a component of RiboMap® Kit) was applied, liquid coverslip was applied, and the slides were incubated at 37° C. for 32 minutes.

Approximately 100 µl (1 drop) of Rabbit anti-DNP followed by liquid coverslip were applied to the slides, which were incubated at 37° C. for an additional 20 minutes at which point the slides were washed twice in Reaction Buffer, 15 µg/ml Goat anti-Rabbit recombinant alkaline phosphatase conjugate (Example 3) was applied, the slides were overlain with liquid coverslip and incubation occurred at 37° C. for 32 minutes. After washing the slides three times in Reaction Buffer, 100 nM Rabbit anti-Goat gold nanoparticle conjugate (Example 1) was applied and incubation proceeded for another 32 minutes. The slides were washed in 0.1 M Tris buffer pH 9.0, silver nitrate and BCIP were applied, liquid coverslip was applied, and incubation proceeded for 32 minutes. Gold chloride and liquid coverslip were applied after the slides were washed with Tris buffer and 4 minutes of incubation followed. After two washes of Tris buffer, silver nitrate was reapplied as well as liquid coverslip and the slides were incubated with 4 more minutes, followed by a Tris buffer wash. Sodium thiosulfate and liquid coverslip were applied, the slides were incubated for 4 minutes, washed with Reaction Buffer, counterstained with Hematoxylin II, washed, and coverslipped for final examination under brightfield microscopy.

Tissue staining showed that when the antibody-nanoparticle conjugate was absent from the detection system, the signal was diffuse and contained a brown hue, making the signal more difficult to observe. Higher magnification was required to observe the signal and staining without the antibody-nanoparticle conjugate did not detect all the positive signals on the tissue. However, when the antibody-nanoparticle conjugate was included in the detection system, the signal became sharp and black. More cells were positive and they were easier to differentiate based on the sharp contrast provided by the black signal and from the signals produced from the increased sensitivity (FIG. 6). Thus, the antibody-nanoparticle conjugate significantly improved the sensitivity of the AP-based detection system, and the system could be used to detect riboprobes.

Previous experiments with the HER2 probe showed the presence of background in the nucleus of the cell (referred to as "dusting"). To determine whether this background was caused by the HER2 probe or the AP silver detection system, the stringency of the wash temperature was increased and varied from 68° C. to 77° C., 82° C. and 87° C. As the temperature of the washes increased, the dusting dissipated, implying that the HER2 probe contained a large amount of DNP-labeled non-specific sequences which annealed to the DNA and caused the background. This further supports the increased sensitivity of the AP silver detection system. The AP silver detection system was able to detect these small haptenated sequences which were non-specifically bound. Although the increase in temperature remedied the amount of dusting observed, it caused some specifically bound probe to separate from its target sequence. An increase in the temperature during stringency washes can thus alleviate background and non-specific staining, but can also diminish specific signal.

Example 5

Biostatistic Comparison of Antibody-Nanoparticle SISH with HRP-Based ISH

Thirty separate breast cancer cases were used to compare the disclosed AP silver detection system to the current HRP SISH kit. Serial sections from each case were evaluated for both HER2 and chromosome 17 (Chr17) using the AP silver detection system and the HRP SISH detection kit as described in Example 4. Once slides were stained and coverslipped, they were blindly evaluated by two different qualified slide readers. The readers were instructed to enumerate the HER2 and Chr17 copy counts by way of the "cowboy method" which requires the reader to estimate the mean copy number for each probe that they are observing. These numbers were recorded and used for analysis. If the signal was too sparse or if the tissue observed could not be enumerated, then the tissue stain was deemed inadequate.

Figure 7B:
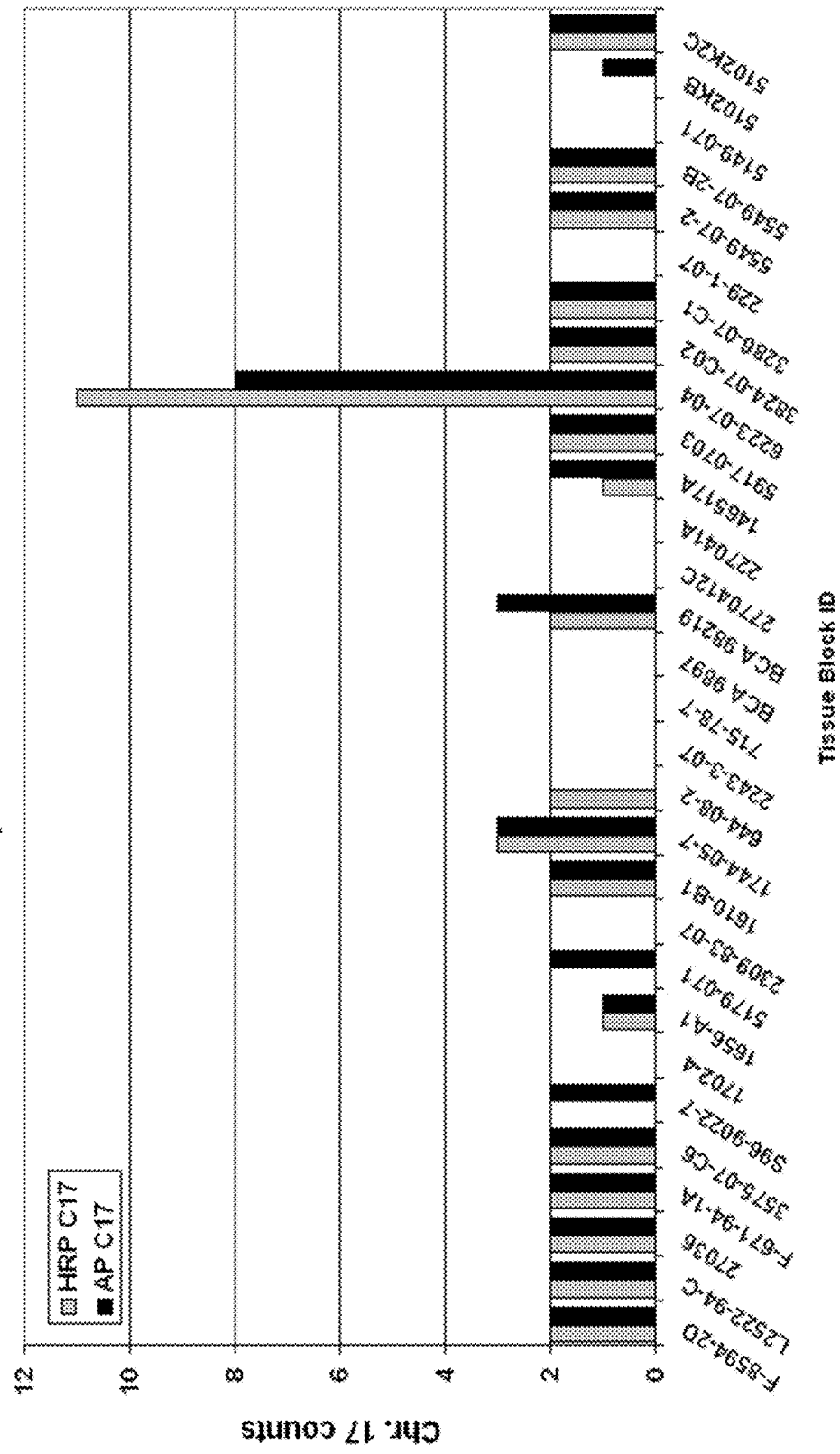
FIGS. 7A and B are a pair of graphs showing Chromosome 17 copy counts from two independent readers using the "cowboy" method on a series of breast cancer tissue samples. The Chromosome 17 probe was detected using HRP-SISH or the disclosed AP silver detection method utilizing an antibody-gold nanoparticle conjugate.
Figure 8B:
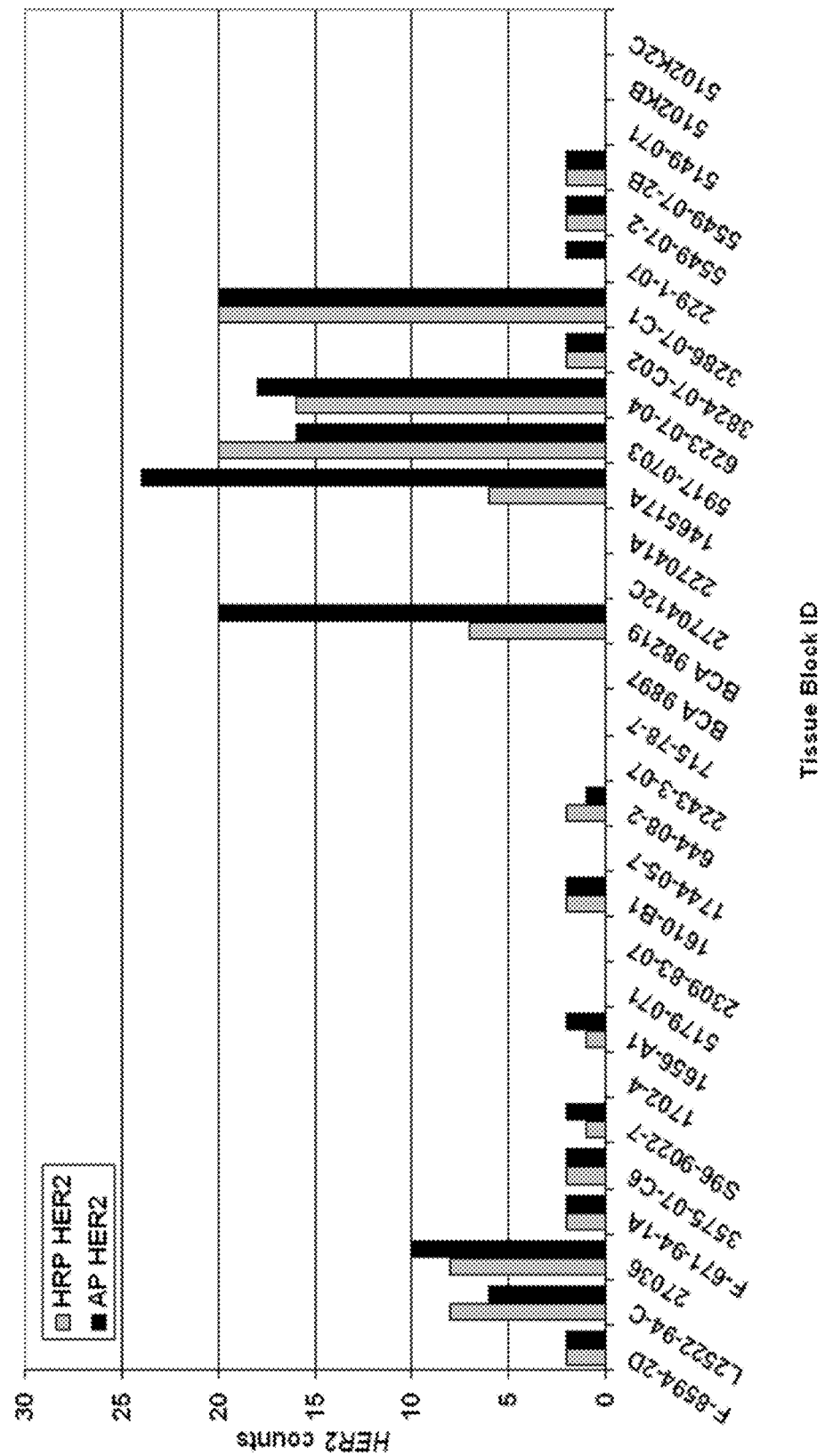
FIGS. 8A and B are a pair of graphs showing HER2 copy counts from two independent readers using the "cowboy" method on a series of breast cancer tissue samples. The HER2 probe was detected using HRP-SISH or the disclosed AP silver detection method utilizing an antibody-gold nanoparticle conjugate.
Figure 9A:
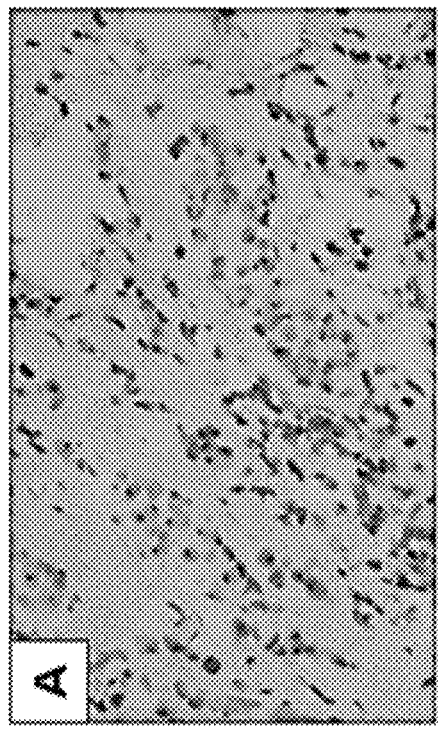
FIGS. 9A-F are a series of digital images of ISH of breast tissue (9A-C) or ZR-75-1 breast cancer cells (9D-F) with a HER2 probe. The HER2 probe was detected by the disclosed AP silver detection method utilizing 100 nM AuNP-antibody conjugate (9A and 9D), 100 nM AuPdNP-antibody conjugate (9B and 9E), or 50 nM AuPdNP-antibody conjugate (9C and 9F).
Figure 9B:
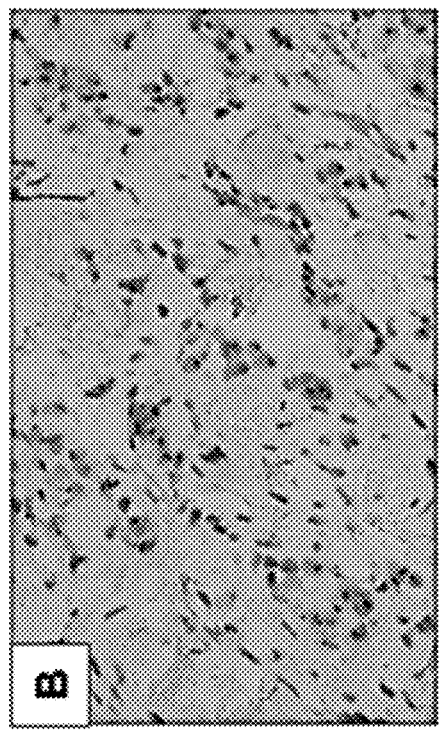
Figure 9D:
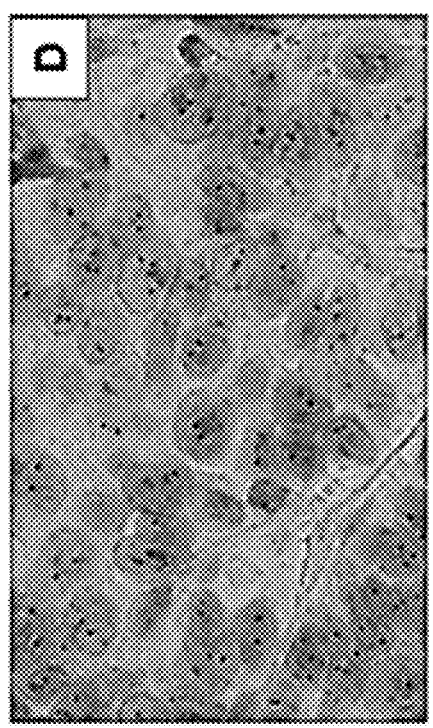
Figure 9C:
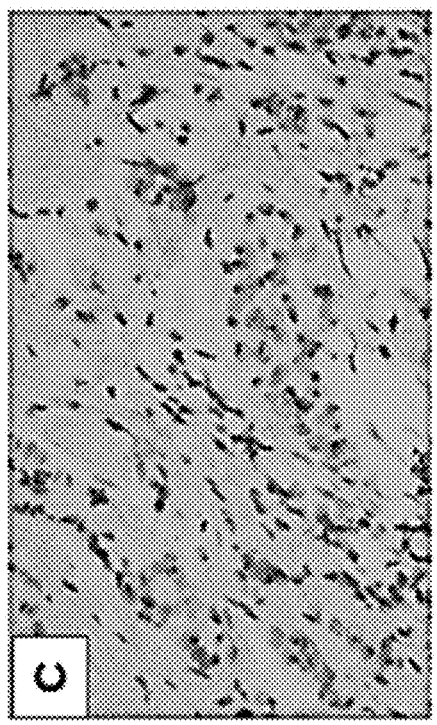
Figure 9E:
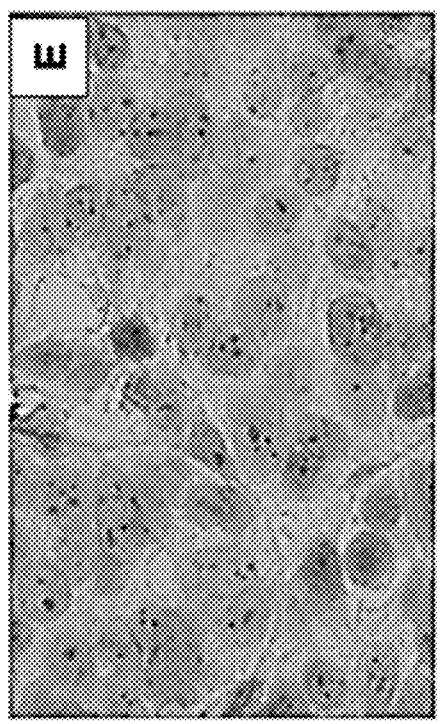
Figure 9F:
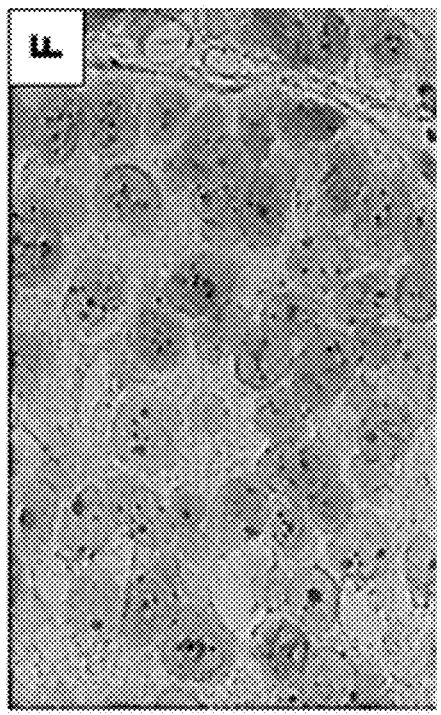

The tissue sample scores for each reader are shown in FIGS. 7A and B (Chr17) and FIGS. 8A and B (HER2). These results were used to calculate the HER2/Chr17 copy ratio. If the copy ratio was greater than or equal to 2, the sample was considered HER2 positive. If either the HER2 or Chr17 sample was deemed inadequate, then the ratio was also deemed inadequate. Results were tabulated to show the distribution of HER2 status determined by the two readers (Tables 3 and 4).

TABLE 3

Concordance table of results from Reader 1

| | | AP Silver Detection | | | |
|---|---|---|---|---|---|
| | | Inadequate | Negative | Positive | Total |
| HRP-SISH | Inadequate | 10 | 4 | 3 | 17 |
| | Negative | 1 | 4 | 0 | 5 |
| | Positive | 1 | 0 | 7 | 8 |
| | Total | 12 | 8 | 10 | 30 |

Table 3 shows that Reader 1 was able to interpret the samples stained with the AP silver detection system that were deemed inadequate when stained with the HRP-SISH kit. Seven cases that were inadequate for HRP-SISH were able to be scored with the AP silver detection system, whereas only two cases that were inadequate for AP silver detection system were able to be scored with the HRP-SISH kit.

TABLE 4

Concordance table of results from Reader 2

| | | AP Silver Detection | | | |
|---|---|---|---|---|---|
| | | Inadequate | Negative | Positive | Total |
| HRP-SISH | Inadequate | 13 | 1 | 0 | 14 |
| | Negative | 1 | 7 | 2 | 10 |
| | Positive | 0 | 0 | 6 | 6 |
| | Total | 14 | 8 | 8 | 30 |

Table 4 shows that Reader 2 scored the slides stained with each system nearly identically, except for 2 cases which were scored negative for HRP-SISH, but positive for AP silver detection system. In each case, the discordance can be attributed to the "cowboy" method by which the reader was instructed to read the slide. This method relies on a more liberal approach of computing the mean copy number by having the reader calculate the number in his or her head. Furthermore, there is no guarantee that the readers referenced the exact same area of tissue when giving their scores.

The scores given by each reader for each detection system were then tabulated to check the reproducibility of the results between the two different readers. Table 5 shows that there was a disagreement between readers when observing tissue samples that were stained with HRP-SISH (kappa=0.5213). The readers agreed more on their scoring when the AP silver detection system was used (Table 6, kappa=0.6429).

TABLE 5

Comparison of HRP-SISH scores between readers

|  |  | Reader 2 | | | |
| --- | --- | --- | --- | --- | --- |
|  |  | Inadequate | Negative | Positive | Total |
| Reader 1 | Inadequate | 12 | 3 | 2 | 17 |
|  | Negative | 0 | 5 | 0 | 5 |
|  | Positive | 2 | 2 | 4 | 8 |
|  | Total | 14 | 10 | 6 | 30 |

TABLE 6

Comparison of AP silver detection scores between readers

|  |  | Reader 2 | | | |
| --- | --- | --- | --- | --- | --- |
|  |  | Inadequate | Negative | Positive | Total |
| Reader 1 | Inadequate | 10 | 2 | 0 | 12 |
|  | Negative | 1 | 6 | 1 | 8 |
|  | Positive | 3 | 0 | 7 | 10 |
|  | Total | 14 | 8 | 8 | 30 |

Example 6

In Situ Hybridization Using Antibody-Gold-Palladium Alloy Nanoparticle Conjugates HER2 in situ hybridization was carried out as in Example 4, except breast tissue or ZR-75-1 breast cancer cell line samples were incubated with 100 nM AuNP-antibody conjugate, 100 nM AuPdNP-antibody conjugate, or 50 nM AuPdNP-antibody conjugate. HER2 staining utilizing the AuPdNP-antibody conjugate was specific, but was weaker than that obtained utilizing the AuNP-antibody conjugate (FIG. 9A-F).

Example 7

Immunohistochemistry Using Antibody-Gold Nanoparticle Conjugates

An assessment of the novel AP-silver detection system versus an HRP detection system was performed on breast carcinoma tissue using a variety of protein biomarkers. The assessment was carried out on breast infiltrating ductal carcinoma tissue samples. Anti-estrogen receptor (ER), anti-Ki-67, and anti-progesterone receptor (PR) were used as the primary antibodies in the protocol without gold toning.

Slide staining was performed on an automated Bench-Mark® XT Instrument as described in Example 4, except for the following changes. Following deparaffinization, the slides underwent standard cell conditioning with CC1, such that the slides underwent a series of 13 reapplications of CC1/liquid coverslip at 100° C., after which the slides were allowed to cool for 3 minutes and rinsed in Reaction Buffer three times. Primary antibodies were added to the appropriate slides for protein target identification; Rabbit anti-Ki67 (VMSI #790-4286), Rabbit anti-ER (SP1; VMSI #790-4325), Rabbit anti-PR (1E2, VMSI #790-4296), Rabbit anti-HER2 (4B5, VMSI #790-2991) on breast tissue samples and Rabbit anti-BCL2 (VMSI #760-4240) on tonsil tissue and the slides were incubated for 16 minutes at 37° C. after application of liquid coverslip.

After the slides were washed with Reaction Buffer twice, 15 µg/ml Goat anti-Rabbit recombinant alkaline phosphatase (Example 3) was added to the slides, followed by an overlay of liquid coverslip and incubation for 16 minutes at 37° C. Then 100 nM Rabbit anti-Goat gold nanoparticle conjugate (Example 1) was applied as in Example 4. The slides were subsequently washed twice in 0.1 M Tris acetate buffer at pH 9.0, then silver nitrate and BCIP were applied, liquid coverslip was reapplied, and the slides were incubated an additional 16 minutes. The slides were washed, gold toned with gold chloride, fixed with sodium thiosulfate (except for samples shown in FIG. 10), and counterstained with Hematoxylin II as previously described. For red counterstaining, nuclear Fast Red (VMSI #280-2119) was incubated on the appropriate slides for 4 minutes. The slides were dehydrated, coverslipped and prepared for viewing by brightfield microscopy.

Figure 10:
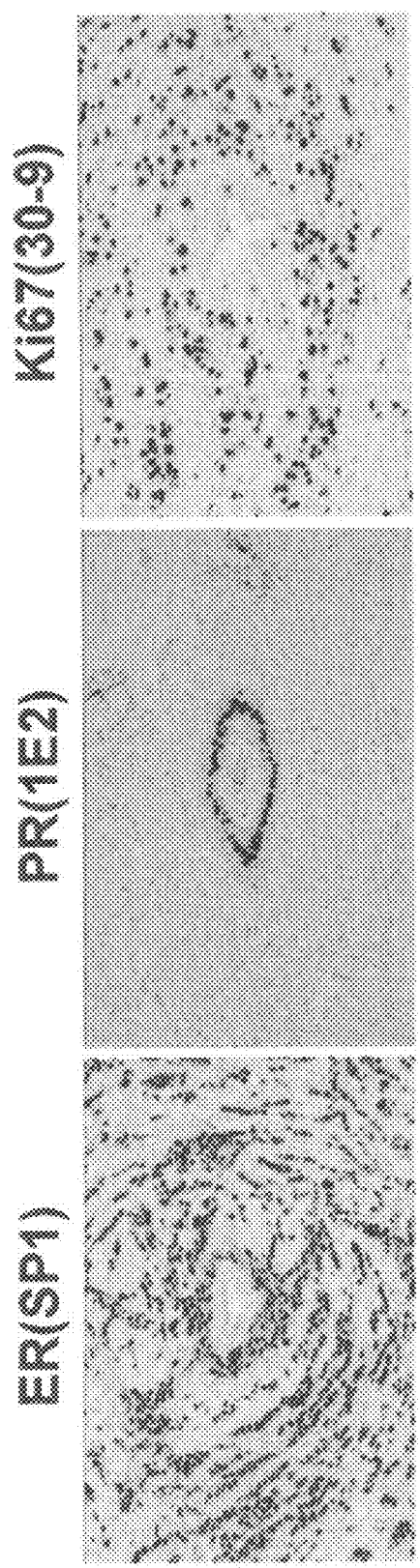
FIG. 10 is a series of digital images of IHC of breast carcinoma tissue with anti-estrogen receptor (ER), anti-progesterone receptor (PR), or anti-Ki67 (Ki67) primary antibody. The primary antibodies were detected using the disclosed AP silver IHC method utilizing an antibody-gold nanoparticle conjugate, omitting gold toning and fixation steps.
Figure 11:
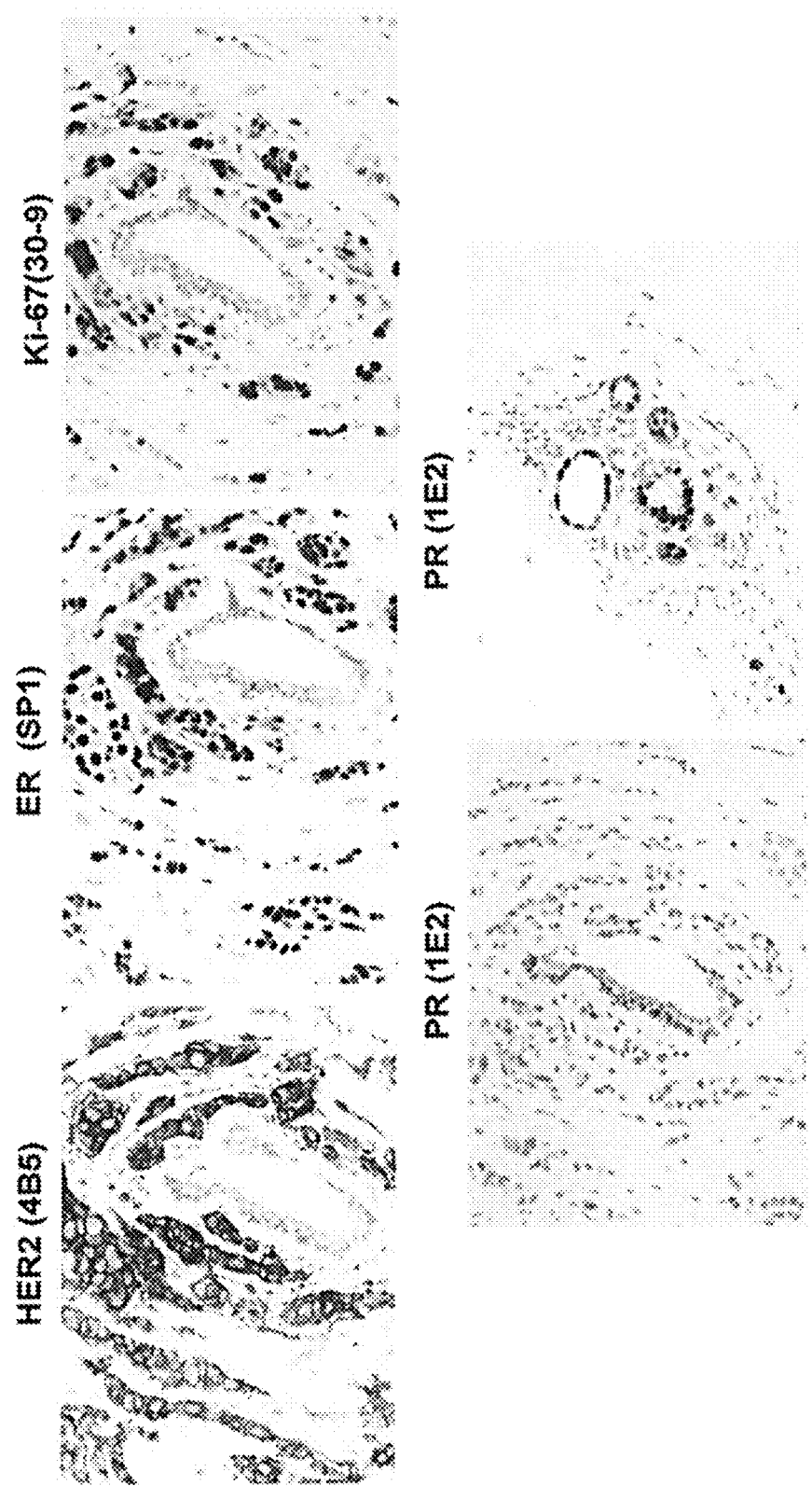
FIG. 11 is a series of digital images of IHC of breast carcinoma tissue with anti-HER2 (HER2), anti-estrogen receptor (ER), anti-Ki67 (Ki67), or anti-progesterone receptor (PR) primary antibody. The primary antibodies were detected using the disclosed AP silver IHC method utilizing an antibody-gold nanoparticle conjugate, including a gold toning step.

All of the samples showed good quantity of signal although there was some background haze (FIG. 10). Anti-HER-2/neu, anti-ER, anti-Ki-67, and anti-PR were used as primary antibodies in the protocol including the gold toning and fixation steps. Specific signal was observed for all the primary antibodies (FIG. 11). The gold toning step significantly improved the quality of the staining by removing the background haze and intensifying the signal.

The novel AP-silver detection system was also assessed on breast carcinoma tissue with a low expression of PR. The new system was compared with the iView™ DAB detection kit (VMSI Cat. No. 760-091), using anti-PR(16) as the primary antibody. The new system demonstrated better sensitivity with no appreciable background.

Figure 12:
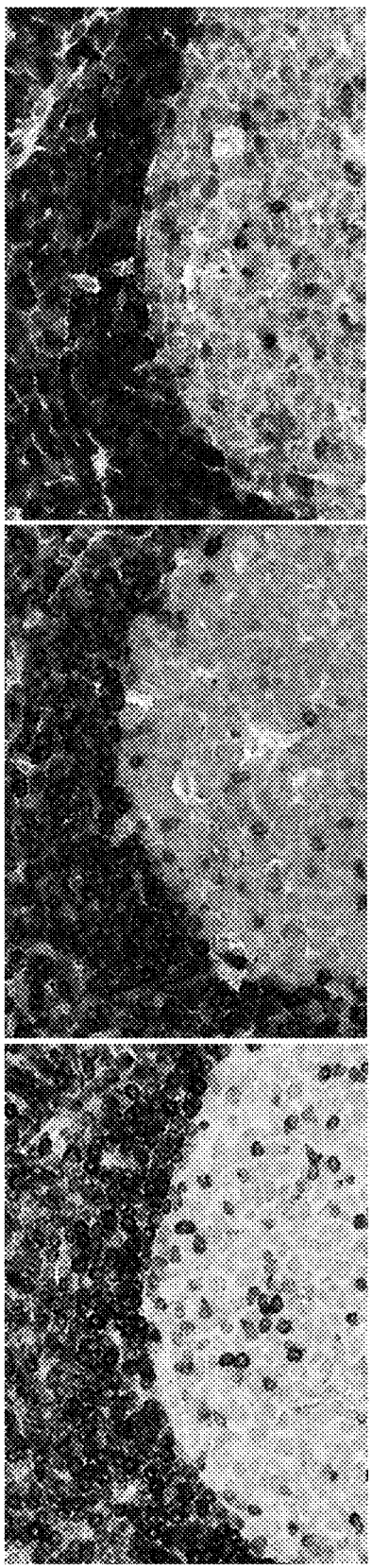
FIG. 12 is a series of digital images of IHC of tonsil tissue with anti-Bcl-2 comparing DAB detection to AP silver using the disclosed antibody-gold nanoparticle conjugate methods. A comparison of counterstains was also performed in conjunction with the AP silver method.

Finally, the novel AP-silver detection system was assessed on tonsil tissue. The new system was compared with the iView™ DAB detection kit, using anti-Bcl-2 as the primary antibody (FIG. 12). Both Fast Red and Bluing/Hematoxylin counterstains were utilized with the AP-silver detection system.

Example 8

Immunohistochemistry Using Antibody-Gold-Palladium Alloy Nanoparticle Conjugates Immunohistochemistry was carried out as in Example 7, except tissue samples were incubated with 100 nM AuNP-rabbit anti-goat antibody conjugate, 100 nM AuPdNP-rabbit-anti-goat antibody conjugate, or 50 nM AuPdNP-rabbit-anti-goat antibody conjugate, or 10 nM AuPdNP-rabbit-anti-goat antibody conjugate. Staining utilizing 100 nM or 50 nM AuPdNP-antibody conjugate was detectable, but not as strong as that obtained utilizing the AuNP-antibody conjugate. Detectable staining was not obtained using 10 nM AuPdNP-antibody conjugate.

Example 9

Exemplary Immunohistochemistry Methods

This example provides exemplary methods for IHC utilizing the disclosed methods including use of antibody-nanoparticle conjugates. A schematic of the method is shown in FIG. 1A. However, one skilled in the art will appreciate that methods that deviate from these specific methods can also be used to successfully perform IHC methods utilizing antibody-nanoparticle conjugates.

Tissue samples are prepared for IHC, including deparaffinization and antigen retrieval and/or protease digestion using conventional methods. The sample is contacted with a primary antibody that specifically binds a target protein (for example, HER2/neu), followed by an alkaline phosphatase (AP)-conjugated secondary antibody (for example, a secondary antibody conjugated to three AP molecules). The sample is then contacted with an antibody conjugated to one or more gold nanoparticles; the antibody is one that specifically binds the secondary antibody. The sample is then contacted with an AP substrate (such as BCIP), followed by a silver compound (for example, silver nitrate). The sample is then subjected to gold toning (for example, treatment with gold chloride), followed by fixation of the signal with a reducing agent (such as sodium thiosulfate). The target protein can be detected by detecting the metal precipitate formed by deposition of silver atoms at the site of the gold nanoparticle. The metal precipitate can be detected, for example, by brightfield microscopy, where it appears as a black deposit.

Example 10

Exemplary In Situ Hybridization Methods

This example provides exemplary methods for ISH utilizing the disclosed methods including use of antibody-nanoparticle conjugates. A schematic of the method is shown in FIG. 1B. However, one skilled in the art will appreciate that methods that deviate from these specific methods can also be used to successfully perform ISH methods utilizing antibody-nanoparticle conjugates.

Tissue samples are prepared for ISH, including deparaffinization and protease digestion using conventional methods. The sample is contacted with a hapten-labeled probe that specifically binds the target nucleic acid molecule (for example, HER2/neu), followed by appropriate stringency washes. The sample is then contacted with a primary antibody that specifically binds the hapten (for example, dinitrophenyl), followed by an alkaline phosphatase (AP)-conjugated secondary antibody (for example, a secondary antibody conjugated to three AP molecules). The sample is next contacted with an antibody conjugated to one or more gold nanoparticles; the antibody is one that specifically binds the secondary antibody. The sample is then contacted with an AP substrate (such as BCIP), followed by a silver compound (for example, silver nitrate).

The sample is then subjected to gold toning (for example, treatment with gold chloride), followed by amplification of the signal (for example, by treatment with a silver compound, such as silver nitrate) and fixation of the signal with a reducing agent (such as sodium thiosulfate). The target nucleic acid molecule can be detected by detecting the metal precipitate formed by deposition of silver atoms at the site of the gold nanoparticle. The metal precipitate can be detected, for example, by brightfield microscopy, where it appears as a black deposit.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method for producing an antibody-nanoparticle conjugate, comprising:
   Providing a reduced intact antibody comprising 2 heavy chains and 2 light chains and having at least one thiol group, wherein the 2 heavy chains are covalently coupled to each other through at least one interchain disulfide bond; the reduced intact antibody is produced by reducing an intact antibody comprising two heavy chains and two light chains with dithiothreitol (DTT) under condition such that at least one thiol group is formed by reduction of at least one of a native interchain disulfide or a native intrachain disulfide of the intact antibody wherein the 2 heavy chains of the reduced intact antibody are covalently coupled to each other through at least one interchain disulfide bond; and
   reacting the reduced intact antibody with an arylphosphine-nanoparticle composite and coupling the reduced intact antibody directly without an intervening linker to the arylphosphine-nanoparticle composite through the at least one formed thiol group through a metal-thiol bond, thereby producing the antibody-nanoparticle conjugate.

2. The method of claim 1, further comprising adjusting reactant stoichiometry and reaction duration to couple two or more nanoparticles to the reduced antibody.

3. The method of claim 2, wherein the antibody-nanoparticle conjugate comprises two to seven nanoparticles.

4. The method of claim 3, wherein the antibody-nanoparticle conjugate comprises five nanoparticles.

5. The method of claim 2, wherein the reactant stoichiometry of the arylphosphine-nanoparticle composite to the reduced antibody is about 7:1, and wherein the number of nanoparticles coupled to the reduced antibody is about five.

6. The method of claim 1, wherein the nanoparticle is about 5 nm or less in diameter.

7. The method of claim 6, wherein the nanoparticle is about 0.5 to about 5 nm in diameter.

8. The method of claim 1, wherein the arylphosphine comprises 1 to 3 sulfonyl groups.

9. The method of claim 8, wherein the arylphosphine is bis-(sulfonatophenyl)phenylphosphine.

10. The method of claim 1, wherein the intact antibody comprises a rabbit, goat, mouse, or anti-hapten antibody.

11. The method of claim 10, wherein the intact antibody is a rabbit anti-goat immunoglobulin G antibody.

12. The method of claim 1, wherein the nanoparticle comprises gold, palladium, platinum, silver, copper, nickel, cobalt, iridium, or an alloy of two or more thereof.

13. The method of claim 1, wherein the arylphosphine-nanoparticle composite is an arylphosphine-gold nanoparticle composite.

14. The method of claim 13, wherein the arylphosphine-gold nanoparticle composite is produced by a method comprising: reducing gold(III) to gold(I); reacting the gold(I) with sodium borohydride to produce gold nanoparticles; and reacting the gold nanoparticles with bis-(sulfonatophenyl)phenylphosphine.

15. The method of claim 14, wherein reducing gold(III) to gold(I) comprises reacting auric acid with triphenylphosphine.

16. The method of claim 1, wherein the antibody-nanoparticle conjugate is an antibody-gold nanoparticle conjugate, and wherein the reduced intact antibody is a reduced rabbit anti-goat immunoglobulin G (IgG) antibody; and the reacting step includes reacting the reduced intact rabbit anti-goat IgG antibody with a bis-(sulfonatophenyl)phenylphosphine (BSPP)-gold nanoparticle composite at a ratio of about 1:7, wherein the BSPP-gold nanoparticle composite is produced by reacting auric acid with triphenylphosphine, thereby producing an auric acid-triphenylphosphine mixture; reacting the auric acid-triphenylphosphine mixture with sodium borohydride to produce gold nanoparticles; and reacting the gold nanoparticles with BSPP, thereby producing the BSPP-gold nanoparticle composite, wherein about five gold nanoparticles are directly conjugated to the reduced intact rabbit anti-goat IgG antibody, thereby producing the antibody-gold nanoparticle conjugate.

17. The method of claim 1, wherein each heavy chain of the intact reduced antibody is coupled to a light chain through an interchain disulfide bond.

18. The method of claim 1, wherein the step of reducing involves reacting the intact antibody with the dithiothreitol for about 25 minutes.

19. The method of claim 1, wherein the step of reducing involves reacting the intact antibody with the dithiothreitol at a temperature of about 4° C.

\* \* \* \* \*